United States Patent
Coleman et al.

(10) Patent No.: US 9,603,600 B2
(45) Date of Patent: Mar. 28, 2017

(54) ACTUATOR FOR DEPLOYABLE IMPLANT

(71) Applicants: James E. Coleman, Dublin (IE);
Christy Cummins, Johnstown Naas (IE)

(72) Inventors: James E. Coleman, Dublin (IE);
Christy Cummins, Johnstown Naas (IE)

( * ) Notice: Subject to any disclaimer, the term of this patent is extended or adjusted under 35 U.S.C. 154(b) by 264 days.

(21) Appl. No.: 14/547,959

(22) Filed: Nov. 19, 2014

(65) Prior Publication Data

US 2015/0142048 A1    May 21, 2015

Related U.S. Application Data

(60) Provisional application No. 61/906,727, filed on Nov. 20, 2013.

(51) Int. Cl.
*A61B 17/12* (2006.01)
*A61B 17/00* (2006.01)
(Continued)

(52) U.S. Cl.
CPC .... *A61B 17/12031* (2013.01); *A61B 17/0057* (2013.01); *A61B 17/12109* (2013.01);
(Continued)

(58) Field of Classification Search
CPC .......... A61B 17/12031; A61B 17/0057; A61B 17/12109; A61B 2090/0807;
(Continued)

(56) References Cited

U.S. PATENT DOCUMENTS 5,324,306 A * 6/1994 Makower ........... A61B 17/0057
604/57
6,461,320 B1 * 10/2002 Yencho ................ A61B 17/11
604/8
(Continued)

FOREIGN PATENT DOCUMENTS

CN    1882293 A    12/2006
CN    102784018 A    11/2012
(Continued)

OTHER PUBLICATIONS

International Search Report and Written Opinion for Application No. PCT/EP2014/075206, 16 pages, dated Feb. 23, 2015.

*Primary Examiner* — Julian W Woo
(74) *Attorney, Agent, or Firm* — Mintz Levin Cohn Ferris Glovsky and Popeo, P.C.

(57) ABSTRACT

Systems and methods are provided for using an actuator to deploy an implant configured to close a tissue puncture or a natural opening in a body. The actuator includes a handle that is rotated in a first direction to deploy a first set of deployable wings of the implant, and that is rotated in a second, opposite direction to deploy a second set of deployable wings of the implant. A guide wire coupled between the implant and the actuator rotates and/or moves axially with the actuator to cause the wings to deploy. After each of the first and second rotation strokes, the handle is prevented from rotating beyond the first and second strokes, respectively. After the wings are deployed to engage tissue therebetween, the handle is operated to eject the implant from the actuator.

24 Claims, 30 Drawing Sheets

(51) Int. Cl.
*A61F 5/00* (2006.01)
*A61B 17/42* (2006.01)
*A61F 2/24* (2006.01)
*A61B 90/00* (2016.01)

(52) U.S. Cl.
CPC .......... *A61F 2/2436* (2013.01); *A61F 2/2457* (2013.01); *A61F 5/0079* (2013.01); *A61B 2017/00389* (2013.01); *A61B 2017/00429* (2013.01); *A61B 2017/00606* (2013.01); *A61B 2017/00623* (2013.01); *A61B 2017/00646* (2013.01); *A61B 2017/00778* (2013.01); *A61B 2017/00986* (2013.01); *A61B 2017/12004* (2013.01); *A61B 2017/12054* (2013.01); *A61B 2017/4233* (2013.01); *A61B 2090/0807* (2016.02); *A61F 2/2418* (2013.01); *A61F 2/2487* (2013.01); *A61F 2220/0008* (2013.01); *A61F 2220/0075* (2013.01); *A61F 2250/001* (2013.01); *A61F 2250/0008* (2013.01); *A61F 2250/0098* (2013.01)

(58) Field of Classification Search
CPC   A61B 2017/00429; A61B 2017/00646; A61B 2017/12004; A61B 2017/00623; A61B 2017/12054; A61B 2017/00389; A61F 2/2436; A61F 2/2457; A61F 5/0079; A61F 2220/0075; A61F 2250/00
See application file for complete search history.

(56) References Cited

U.S. PATENT DOCUMENTS

| | | |
|---|---|---|
| 6,942,674 B2 * | 9/2005 | Belef .................. A61B 17/0057 606/139 |
| 7,625,392 B2 | 12/2009 | Coleman et al. |
| 2006/0122647 A1 | 6/2006 | Callaghan et al. |
| 2013/0165963 A1 | 6/2013 | Coleman et al. |

FOREIGN PATENT DOCUMENTS

| | | |
|---|---|---|
| CN | 102824199 A | 12/2012 |
| WO | 2012163820 A2 | 12/2012 |

* cited by examiner

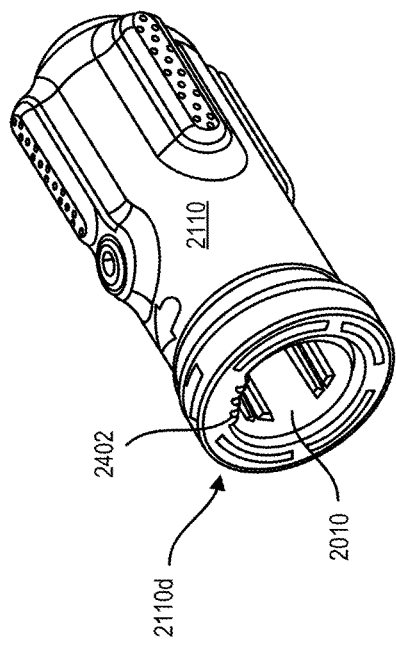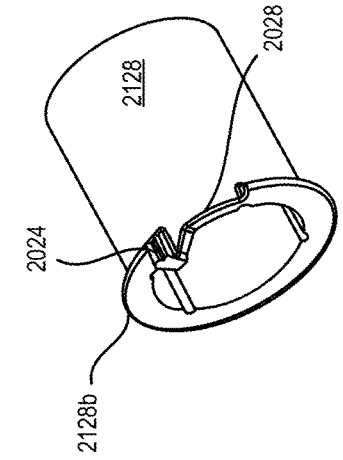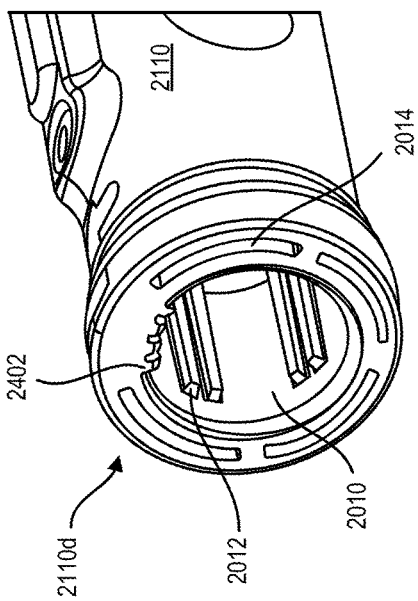

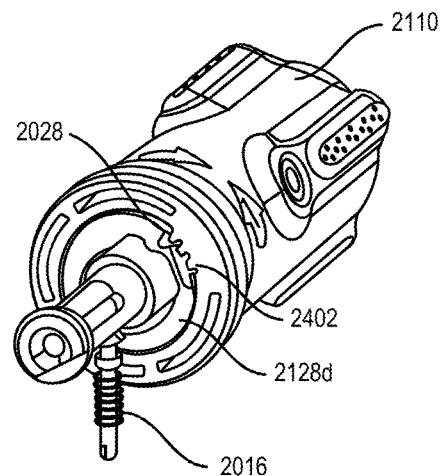
FIG. 31A
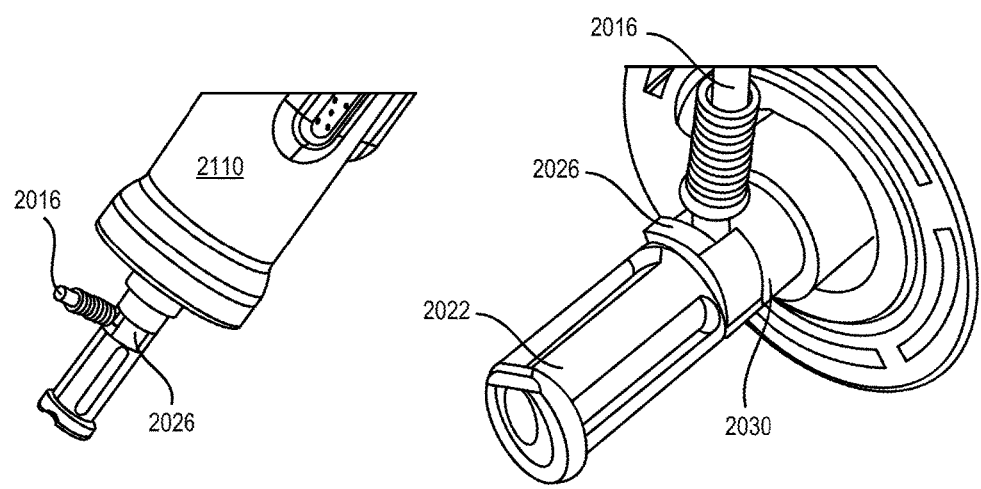
FIG. 31B
FIG. 31C

ACTUATOR FOR DEPLOYABLE IMPLANT

CROSS REFERENCE

The present application claims priority to U.S. Provisional Application No. 61/906,727 entitled "Surgical Implant Devices, Systems, and Methods," filed Nov. 20, 2013, which is hereby incorporated herein by reference in its entirety.

FIELD

Systems and methods are provided for using actuators for a deployable implant.

BACKGROUND

Many surgical procedures involve creating punctures in tissue at a surgical site. A puncture in a patient's blood vessel can be created during catheterization and interventional procedures, such as angioplasty or stenting. Furthermore, some surgical procedures may require closing or narrowing natural openings in a subject's body, such as procedures involving a heart valve repair, narrowing of a pylorus, or occluding a fallopian tube. It can also be desirable to seal openings that form in a body related to a defect or disease.

Various apparatuses have been suggested for percutaneously sealing openings existing or created in a subject's body. For example, biodegradable plugs, sutures, surgical fasteners, and other devices have been employed to close openings in the body. However, many of the existing approaches have certain drawbacks.

Accordingly, improved systems and methods for closing openings in a subject's body are needed. There also remains a need for improved systems and methods for deploying devices for closing an opening in a simple and effective manner.

SUMMARY

The present disclosure is generally related to an actuator for deploying a closure device or an implant. In one aspect, an actuator is provided that includes a housing having proximal and distal portions, the proximal portion being rotatable relative to the distal portion about a longitudinal axis of the housing extending through the proximal and distal portions, a guide tube coupled to the distal portion and having a distal end configured to engage an implant, and a guide wire extending through the guide tube, the distal portion, and the proximal portion, the guide wire being fixedly coupled to the proximal portion such that rotation of the proximal portion causes the guide wire to rotate. The proximal portion of the housing is configured to slide axially away from the distal portion after the proximal portion is rotated through a rotation stroke.

The actuator can vary in any number of ways. In some embodiments, the actuator includes a biasing mechanism configured to cause the proximal portion to slide axially away from the distal portion at the end of the rotation stroke. The rotation stroke includes a first rotation stroke in which the proximal portion is rotated in a first direction about the longitudinal axis. The rotation stroke further includes a second rotation stroke in which the proximal portion is rotated in a second opposite direction about the longitudinal axis. The proximal portion of the housing can be configured to slide axially away from the distal portion at the end of each of the first rotation stroke and the second rotation stroke.

The proximal portion can be configured to rotate in a first direction to deploy a first portion of an implant, and in a second opposite direction to deploy a second portion of an implant. The proximal portion is configured to be prevented from rotating in the first direction after the first portion of the implant is deployed, and the proximal portion is configured to be prevented from rotating in the second direction after the second portion of the implant is deployed. In some embodiments, the proximal portion is configured to be prevented from rotating in the first and second directions after the first and second portions of the implant are deployed.

The actuator can further include a locking mechanism configured to prevent rotation of the proximal portion after an implant coupled to the guide tube is deployed. The locking mechanism can include a tab that blocks movement of a guide pin on the distal portion of the actuator. The distal portion can include a guide pin that extends into a track for guiding rotational movement of the proximal portion. The track can include a first portion extending radially about the longitudinal axis, a second portion extending radially about the longitudinal axis, and a third portion extending longitudinally relative to the longitudinal axis and extending between the first and second portions.

The actuator can further include a lever coupled to the housing thereof and operable to move the proximal portion of the housing axially away from the distal portion of the housing and to detach at least a portion of an implant from the guide tube.

In another aspect, an actuator assembly for deploying an implant is provided that includes a handle assembly having a guide tube extending distally therefrom, a guide wire extending through the guide tube and at least a portion of the handle assembly, a rotatable actuator coupled to the handle assembly and configured to rotate the guide wire, a locking mechanism configured to prevent rotation of the rotatable actuator after an implant coupled to the guide tube is deployed. The guide tube has a distal end configured to engage an implant.

The actuator assembly can vary in any number of ways. For example, in some embodiments, the actuator can include a lever coupled to the handle assembly and operable to detach at least a portion of an implant from the guide tube. In some embodiments, the actuator can include a biasing mechanism configured to bias the rotatable actuator in a proximal direction relative to the housing.

The rotatable actuator, which can be located at a proximal end of the handle assembly, can be configured to rotate in a first direction to deploy a first portion of an implant, and in a second opposite direction to deploy a second portion of an implant. The rotatable actuator can also be configured to slide axially away from a distal portion of the handle assembly. The actuator can slide in this manner at the end of a rotation stroke. The rotatable actuator is prevented from rotating in the first direction after the first portion of the implant is deployed, and the rotatable actuator is prevented from rotating in the second direction after the second portion of the implant is deployed.

In another aspect, a method for deploying an implant is provided that includes manipulating a delivery device to position an implant at a surgical site, rotating an actuator of a handle assembly of the delivery device through a first rotation stroke to deploy a first portion of the implant, and rotating the actuator of the handle assembly through a second rotation stroke to deploy a second portion of the implant, the actuator being prevented from rotating upon completion of the second rotation stroke.

The actuator can be a proximal portion of the handle assembly. The actuator can be rotated in a first direction for the first rotation stroke, and the actuator can be rotated in a second opposite direction for the second rotation stroke. In some embodiments, the actuator can slide longitudinally upon completion of the first rotation stroke. The actuator can also slide longitudinally upon completion of each of the first rotation stroke and the second rotation stroke.

The method can vary in a number of ways. For example, the method can include rotating a lever on the handle assembly to detach at least a portion of the implant from the delivery device.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings:

FIG. 23 is a perspective view of a body rear of a housing of the handle assembly of FIG. 22;

FIG. 24 is a detailed perspective view of the body rear of the housing of FIG. 23, illustrating a body rear tab thereof;

FIG. 25 is a perspective view of a ring connector of the actuator of FIG. 22;

FIG. 31A is a perspective view of a body rear of a housing of the handle assembly of FIG. 30 following deployment of a first set of wings of an implant;

FIG. 31B is another perspective view of a body rear of a housing of the handle assembly of FIG. 30 following deployment of the first set of wings of an implant;

FIG. 31C is another perspective view of a body rear of a housing of the handle assembly of FIG. 30 following deployment of the first set of wings of an implant;

DETAILED DESCRIPTION

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present embodiments is defined solely by the claims. Further, the features illustrated or described in connection with one exemplary embodiment may be combined with the features of other embodiments. Such modifications and variations are intended to be included within the scope of the described embodiments.

Methods and devices for deploying an implantable puncture closure device, or an implant, are provided. In particular, the described techniques utilize actuator devices that are actuated to deploy an implant at a surgical site. The implant can include deployable proximal and distal wings configured to expand to engage tissue therebetween. An actuator device can be removably attached to the implant via a guide member and it can be configured to be rotated to cause the implant to deploy to thereby close an opening in a subject's body.

In certain exemplary methods, a proximal or rear portion of the actuator device can be rotated with respect to a distal or front portion thereof. Rotation of the rear portion in a first direction via a first rotation stroke causes a first set of wings of the implant to deploy, and rotation of the rear portion in a second, opposite direction via a second rotation stroke causes second wings of the implant to deploy. The actuator can be configured so that the first rotation stroke is limited to a predetermined distance of rotation, which is effective to deploy the first set of wings. Once the first rotation stroke is complete, further rotation in the first direction is not possible. Similarly, once the second rotation stroke is complete and the second set of wings is deployed, further rotation in the second direction is not possible. After the first and second sets of wings are deployed, the actuator device can be manipulated to eject the implant by separating the implant from the actuator device.

Accordingly, the described actuator devices allow deploying an implant via simple rotation strokes that are controllable due to a configuration of the actuator. In this way, a surgeon can utilize the actuator in accordance with the described embodiments to deploy the implant in a simple and effective manner.

The described devices and methods can be used to deploy an implant or closure device to close a puncture wound, a natural opening in a subject's body, or an opening related to a disease or defect.

Figure 1:
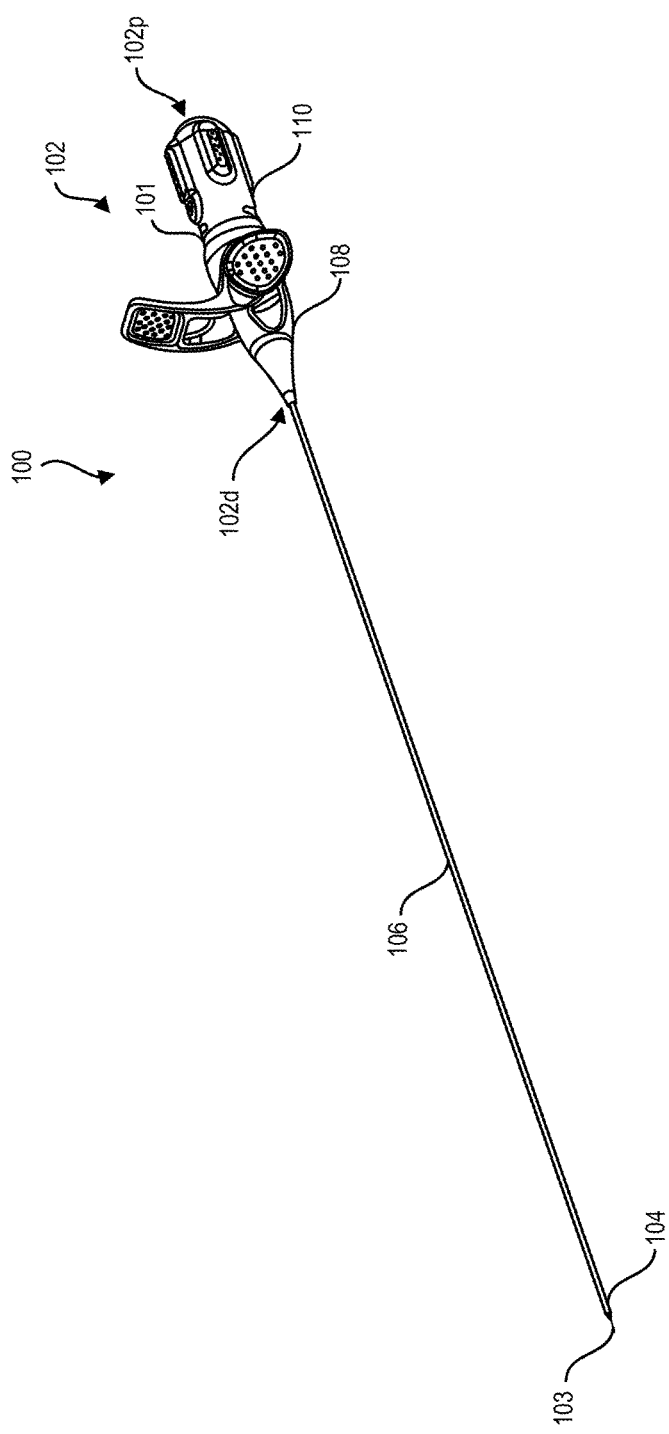
FIG. 1 is a perspective view of one exemplary embodiment of an actuator device having an implant disposed on a distal end thereof.
Figure 2:
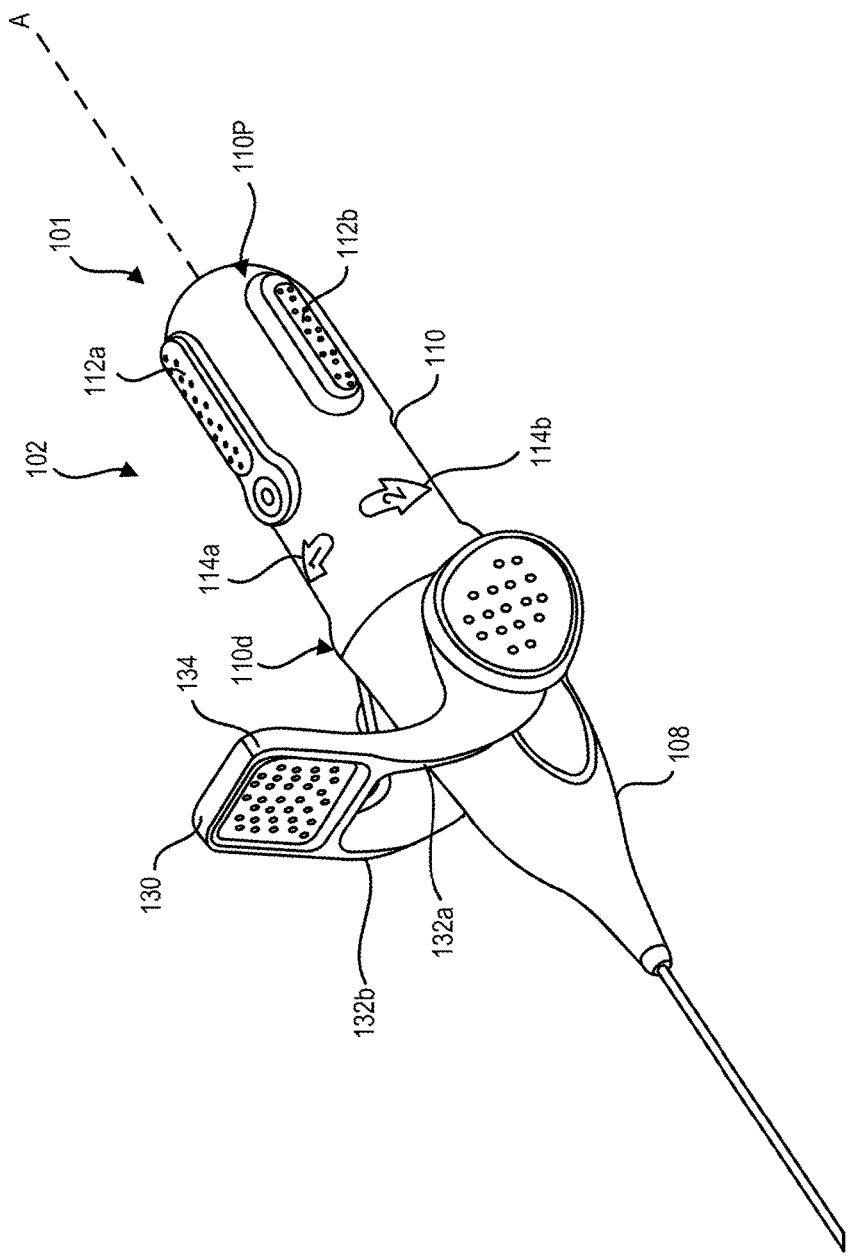
FIG. 2 is perspective view of a handle assembly of the actuator of FIG. 1.

FIGS. 1 and 2 illustrate one exemplary embodiment of an actuator 100 including a handle assembly 102 for deploying an implant or closure device 104. The actuator 100 is sequentially rotatable in first and second directions via respective first and second rotation strokes to deploy first and second portions of the implant 104. The actuator 100 is rotatable so that its rear portion is configured to be rotated with respect to the front portion, and, as a result of each rotation stroke, the rear portion also slides axially away from a front portion. A biasing mechanism, such as a compression spring disposed in the front portion, is configured to apply force to the rear portion to bias it proximally, thus helping to effect the axial motion as the rear portion is rotated.

A ring connector coupled to the front portion can selectively engage with the rear portion as the rear portion rotates, to control movement of the rear portion with respect to the front portion. In particular, movement of the rear portion is controlled so that the actuator 100 is able to rotate only a first distance during a first rotation stroke, which is effective to deploy a first portion of the implant. Further, the rear portion is controlled so that the actuator 100 is able to rotate only a second distance during a second rotation stroke, which is effective to deploy a second portion of the implant. After the first and second portions of the implant 104 are deployed, the actuator 100 is manipulated to eject the implant 104 therefrom.

Accordingly, the actuator 100 is configured to deploy the implant 104 via three strokes, for example, a first rotation stroke deploys distal wings of the implant 104, a second rotation stroke deploys proximal wings of the implant 104, and a third stroke ejects the implant. Each stroke is performed through a controlled movement so that a rotational distance of the stroke is defined by the configuration of components of the actuator 100.

As shown in FIGS. 1 and 2, the handle assembly 102 is generally cylindrical and has a distally tapered distal end 102d. As shown in FIG. 1, the distal end 102d of the handle assembly 102 can be removably coupled to the implant 104 via an elongate shaft or guide tube 106.

The handle assembly 102 includes a housing 101 having a distal portion or body front 108 and a proximal portion or body rear 110 coupled to the body front 108. The body rear or actuator portion 110 is rotatable and axially slidable relative to the body front 108 about a longitudinal axis A of the housing 101 extending through the proximal and distal portions 110, 108. As used herein, the term "proximal" end or portion refers to an end or portion that is nearest to a person operating the handle assembly 102, and the term "distal" end or portion refers to an end or portion that is closer to a forward end of the implant 104.

The body rear 110 can have a variety of configurations. In the illustrated exemplary embodiment, the body rear 100 has a generally cylindrical shape. In the example illustrated, a proximal end 110p of the body rear 110 can be rounded and a distal end 110d thereof configured to mate with the body front 108 can have an enlarged outer diameter. One skilled in the art will understand, however, that the body rear 100 can have any other configurations, as the described embodiments are not limited in this respect.

Figure 3:
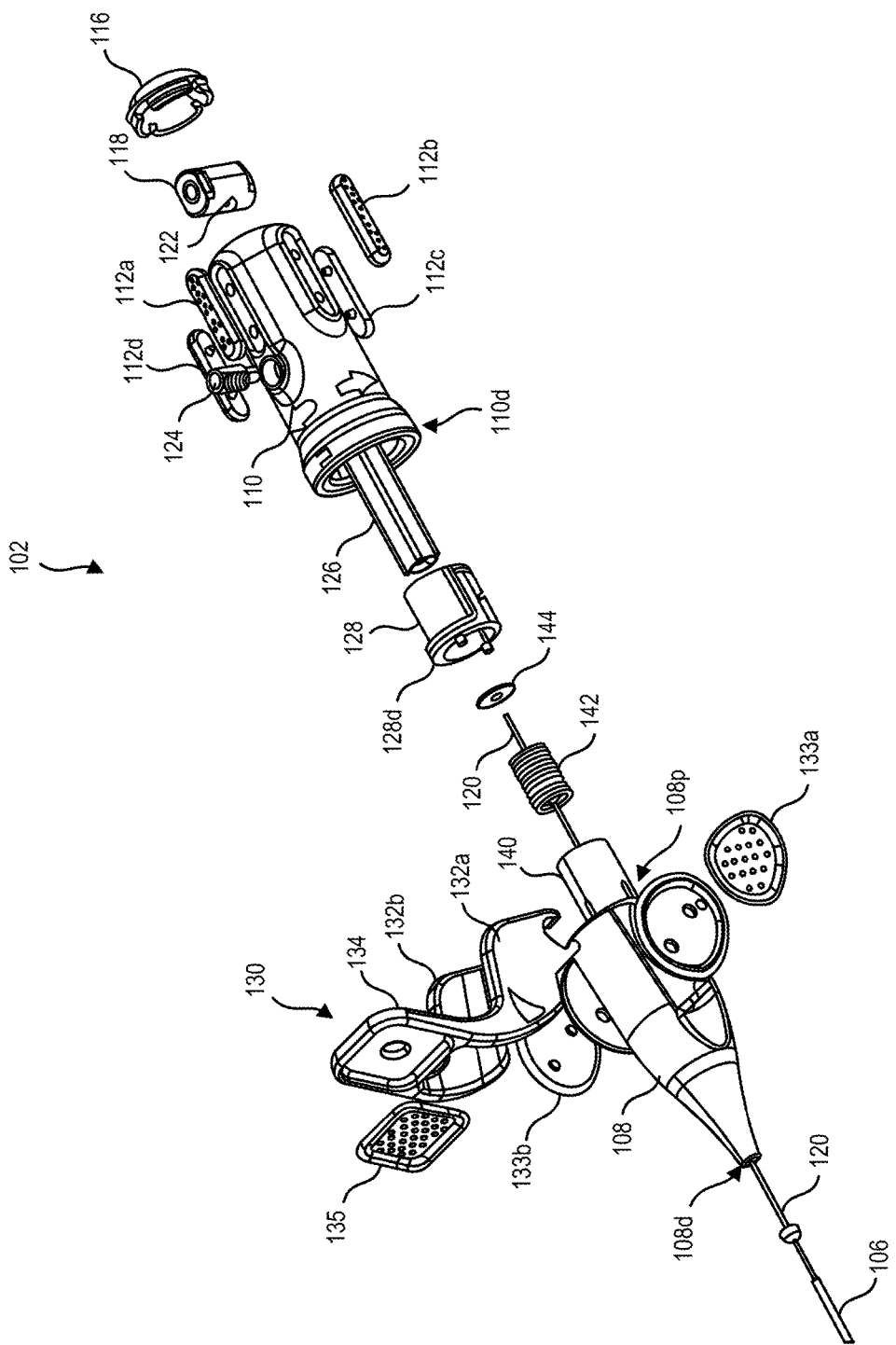
FIG. 3 is an exploded view of the handle assembly of the actuator of FIG. 2.

As shown in FIGS. 2 and 3, the body rear 110 includes on an outer surface thereof suitable features that facilitate gripping of the body rear 110 during operation of the actuator 100. For example, in the illustrated embodiment, the body rear 110 includes one or more gripping portions 112a, 112b, 112c, 112d shown in FIGS. 2 and 3 (only gripping portions 112a and 112b are shown in FIG. 2). The body rear 110 is configured to rotate with respect to the body front 108, as discussed in more detail below.

To facilitate operation of the handle assembly 102, the body rear 110 can include markings 114a, 114b which indicate a direction of rotation of the body rear 110 to deploy a respective set of wings. For example, in the illustrated exemplary embodiment, the marking 114a indicates a first direction (e.g., a clockwise direction) in which the body rear 110 is configured to rotate with respect to the body front 108 to deploy a first set of wings of the implant 104, and the marking 114b indicates a second direction (e.g., a counter-clockwise direction) in which the body rear 110 is configured to rotate with respect to the body front 108 to deploy a second set of wings of the implant 104. It should be appreciated that the handle assembly 102 and the body rear 110 can include any other suitable surface features that facilitate gripping and operation of the handle assembly 102.

The body rear 110 can be hollow. As shown in FIG. 3, illustrating an exploded view of the handle assembly 102, the body rear 110 has a cap 116 configured to enclose a proximal end 110p thereof. As also shown in FIG. 3, the body rear 110 includes an internally threaded insert 118 that can receive therein a guide wire 120. The guide wire 120 can pass through an opening 122 in the insert 118 and can be locked therein with a locking mechanism, such as a lock screw 124. The lock screw 124 can have an external thread formed around the outer surface thereof and configured to engage with the internal thread formed in the insert 122.

As also shown in FIG. 3, the body rear 110 can include an inner shaft or actuator base 126 configured to fit within the body rear 110 and extend through at least a portion of the body front 108. The inner shaft 126 abuts a compression spring 142 that is attached to the body front 108 and is configured to apply a constant force to the inner shaft 126. The compression spring 142 can be attached to the body front 108 in any suitable manner.

The body rear 110 can receive therein a ring connector or a body front ring 128 coupled to the body front 108 and configured to be advanced over the inner shaft 126. The ring connector 128 can be configured to include features so as to control an amount of rotational movement of the body rear 110 in first and second directions to deploy first and second portions of an implant, respectively. For example, the ring connector 128 can include slots or channels and other features configured to interact (e.g., receive and retain therein) features formed in the body rear 110 to guide and limit rotation of the body rear 110 with respect to the body front 108.

Figure 4:
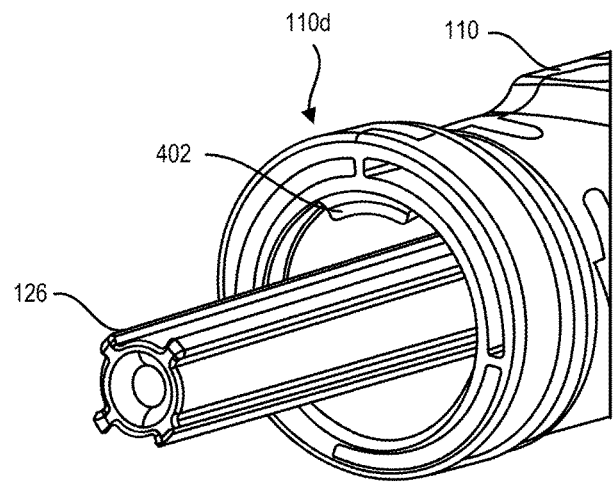
FIG. 4 is a detailed perspective view of the handle assembly of FIG. 2, illustrating a body rear tab thereof.

The ring connector 128 controls rotational movement of the body rear 110 so that, when the body rear 110 is rotated, engaging features formed thereon move within the channels or slots, or other retaining features (e.g., stop surface(s)) formed in the ring connector 128. In the illustrated embodiment, the engaging features formed in the body rear 110 include a body rear tab 402 formed on an inner surface of the body rear 110 at a distal end 110d thereof, as shown in FIG. 4.

The body front 108 can have a variety of configurations. In the illustrated exemplary embodiment, the body front 108 has a generally cylindrical shape. As shown in FIGS. 2 and 3, a distal portion of the body front 108 can be distally tapered such that a distal end 108d thereof has a gradually decreasing outer diameter. As also shown, the body front 108 has a lever 130 pivotably attached thereto. The lever 130 can be coupled to a proximal portion of the body front 108 such that its arms 132a, 132b extend from the body front 108 transversely to a longitudinal axis A of the handle assembly 102. The arms 132a, 132b can be connected via a middle portion 134 that can be held (e.g., by a surgeon) to move the lever 130 with respect to the handle assembly 102. The arms 132a, 132b and the middle portion 134 can have on outer surfaces thereof respective gripping portions 133a, 133b, 135 that facilitate gripping of the lever 130 by an operator of the actuator 100 (e.g., a surgeon). The handle assembly 102 can include marking(s) or other features facilitating operation of the lever 130 by the surgeon, as well as any other markings.

As shown in FIG. 3, the body front 108 has an inner tube 140 received therein, a compression spring 142 configured to sit within the inner tube 140, and one or more washers 144 configured to be disposed between the compression spring 142 and the inner shaft 126 and/or between the inner tube 140 and the compression spring 142 (not shown). The compression spring 142 can be configured to apply constant force to the distal end of the inner shaft 126 such that the constant force is applied to the distal end of the body rear 110. One skilled in the art will appreciate that the body front 108 can include any other suitable components that are not shown herein.

Figure 5:
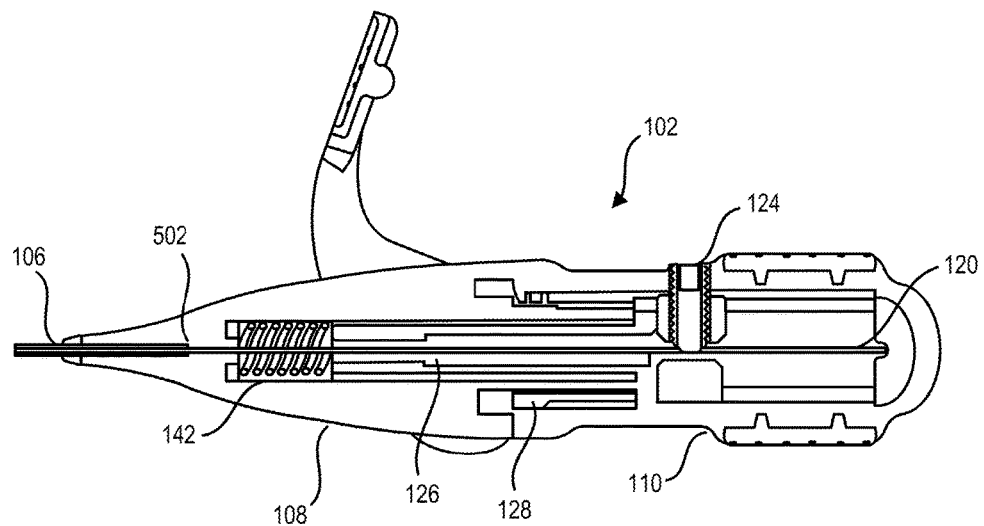
FIG. 5 is a side cross-sectional view of the handle assembly of FIG. 2 prior to deployment of wings of the implant associated therewith.

Referring back to FIG. 1, the actuator 100 can be coupled to an elongate guide tube 106 having a distal end configured to removably engage the implant 104. A proximal end of the guide tube 106 can be coupled to the body front 108 of the handle assembly 102. The actuator 100 can be configured to accept a guide wire 120 that extends through the guide tube 106 as shown in FIG. 3. As shown in FIG. 5, prior to deployment of the implant 104, the guide wire 120 extends through the guide tube 106, the body front 108, and the body rear 110. In the illustrated embodiment, the guide wire 120 extends through the handle assembly 102 so that it does not protrude from the proximal end 102p of the handle assembly 102.

In the illustrated embodiment, the guide wire 120 is configured as an elongate wire or tube formed from a suitable metal such as, for example, stainless steel, titanium, or Nitinol®. The guide wire 120 can have a diameter of, for example, from about 0.1 millimeters (mm) to about 2 mm, and can have a length of, for example, from about 150 mm to about 500 mm. It should be appreciated, however, that the guide wire 120 can have any suitable dimensions, as the described embodiments are not limited in this respect.

As shown in FIG. 5, the guide wire 120 can be fixedly coupled to the body rear 110 so that rotational and/or axial movements of the body rear 110 cause the guide wire 120 to move in the same manner. While a person skilled in the art will appreciate that a variety of locking feature can be used to fix the guide wire 120, in one example, the guide wire 120 is fixedly coupled to the body rear 110 via a lock screw 124, as shown in FIG. 3. The guide wire 120 can extend through the guide tube 106 such that the guide wire 120 is coupled to the implant 104 at a distal end thereof and can be used in deployment of the implant 104, as discussed in more detail below.

A variety of implants can be used with the actuator described herein. By way of example, an implant described herein (e.g., implant 104) can include one or more components configured as described at least in U.S. Pat. No. 7,625,392 entitled "Wound Closure Devices and Methods," issued Dec. 1, 2009; U.S. Pat. No. 8,197,498 entitled "Gastric Bypass Devices and Procedures," issued Jun. 12, 2012; U.S. Patent Application Publication No. 2009/0105733, entitled "Anastomosis Devices and Methods," filed Oct. 22, 2007; and U.S. Patent Application Publication No. 2013/0165963, entitled "Devices and Methods for Occluding or Promoting Fluid Flow," filed Dec. 21, 2011, the contents of each of which are incorporated herein by reference in their entireties.

Figure 6A:
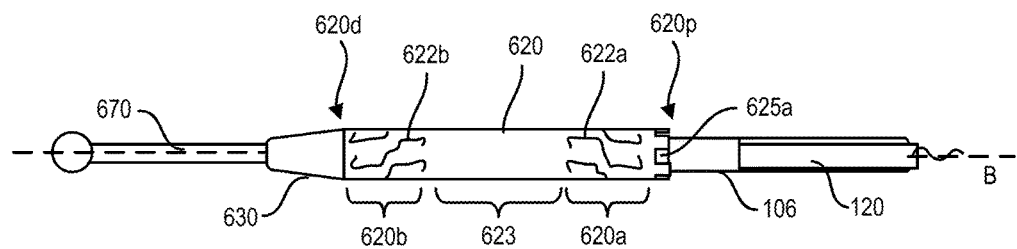
FIG. 6A is a side cross-sectional view of an implant prior to deployment of proximal and distal wings thereof and prior to ejection thereof from the actuator device.
Figure 6B:
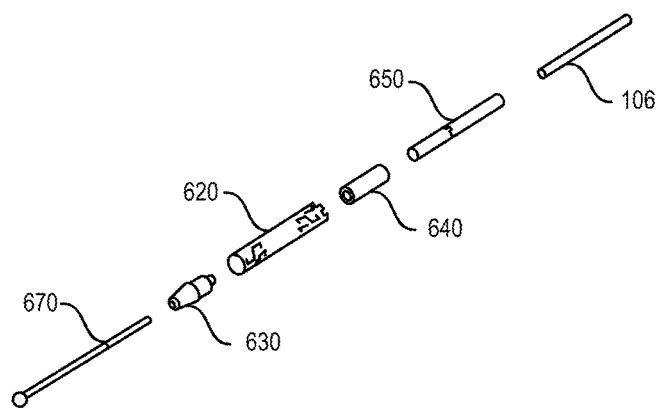
FIG. 6B is a perspective exploded view of the implant of FIG. 6A.
Figure 6C:
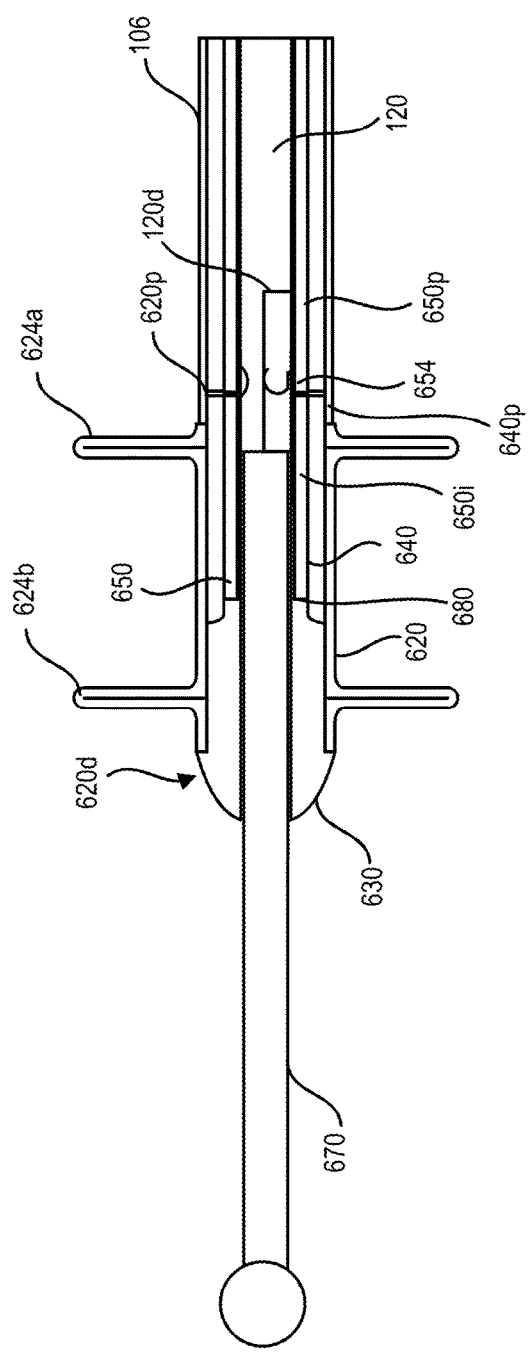
FIG. 6C is a side cross-sectional view of an implant after deployment of proximal and distal wings thereof and prior to ejection thereof from the actuator device.

FIGS. 6A to 6C illustrate one exemplary embodiment of an implant 104 that can be deployed using the actuator described hereon. As shown in FIGS. 6A and 6B, the implant 104 includes a generally elongate tubular body 620 having proximal and distal ends 620p, 620d and a number of components attached thereto and/or disposed therein. These components can include, for example, a guide member or core pin 630, a slide tube 640, an ejection tube 650, a distal tip or guide tip 670, and an insertion shaft or guide tube 106.

The elongate tubular body 620 includes proximal and distal portions 620a, 620b that are configured to expand to engage tissue therebetween. As shown in FIG. 6A, the proximal and distal portions 620a, 620b each include a plurality of slits 622a, 622b formed therein and configured to allow portions of the elongate tubular body 620 between the pluralities of slits 622a, 622b to radially expand. A mid-portion 623 of the tubular body 620, located between the proximal and distal portions 620a, 620b are configured to be positioned within a tissue puncture or hole to be sealed using the implant 104. The mid-portion 623 can have a fixed or adjustable length that corresponds to a thickness of tissue walls. In some embodiments, the mid-portion 623 can be slit-free.

The slits 622a, 622b in the proximal and distal portions 620a, 620b can extend in any direction, and each portion 620a, 620b can include any number of slits. The slits 622a, 622b of the proximal and distal portions 620a, 620b can be configured such that material between the slits 622a, 622b can extend outward away from a central axis B of the tubular body 620 when the tubular body 620 is axially rotated and/or compressed. As a result, one or more wings 624a, 624b will form in each of the distal and proximal portions 620a, 620b to engage tissue therebetween. The implant 104 can also include tabs 625a in the proximal portion 620a thereof to aid in forming the wings. Tabs can likewise be formed in distal portion 620b if desired. In some embodiments, the wings 624a, 624b can include tissue-engaging tangs (not shown) that extend generally perpendicular to the formed wing and provide assistance in maintaining a location of the implant 104.

In an exemplary embodiment, as shown in FIGS. 6A and 6B, the slits 622a in the distal portion 620b can extend in a first direction around a circumference of the elongate tubular body 620, and the slits 622b in the proximal portion 620b can extend in a second, opposite direction around the circumference of the elongate tubular body 620. Such a configuration allows the tubular body 620 to be rotated in a first direction to cause only one of the proximal and distal portions 620a, 620b to radially expand, and then to be rotated in a second, opposite direction to cause the other one of the proximal and distal portions 620a, 620b to radially expand. The proximal and distal portions 620a, 620b can be adapted to move towards one another as they expand upon rotation and are compressed into shape, thereby allowing the wings to engage tissue therebetween.

As shown in FIGS. 6A and 6C, the distal end 620d of the tubular body 620 is coupled to a guide member or core pin 630, which can assist in guiding the implant 104 to its desired location. In the illustrated embodiment, the core pin 630 extends into a portion of the elongate tubular body 620.

The core pin 630 can be generally hollow and can include a bore extending therethrough, or it can be solid or closed.

The implant 104 can further include a slide tube 640 which can be disposed within the outer elongate tubular body 620. The slide tube 640 can be configured to slide within the implant 104 and assist in the actuation of the implant 104. In the illustrated embodiment, the slide tube 640 is generally cylindrical in shape and includes a bore therethrough so that the slide tube 640 can receive a shaft, such as the ejection tube 650, along which the slide tube 640 can slide, as shown in FIG. 6C. In one embodiment, as shown in FIG. 6C, when the proximal wings 624a are formed, the slide tube 640 remains disposed across an opening below the formed wings 624a to thereby occlude fluid from passing into the expanded wings 624a. Likewise, the core pin 630 can occlude fluid from passing into the expanded distal wings 624b. As a result, in some embodiments, fluid traveling through the internal bore of the implant cannot migrate through the slots in the base of the distal and proximal wings 624b, 624a as they are sealed by the core pin 630 and the slide tube 640. However, it should be appreciated that the slide tube 640 can be disposed within the tubular body 620 in any other manner.

In one embodiment, as shown in FIG. 6C, a proximal end 640p of the slide tube 640 can be coupled to the proximal end 620p of the tubular body 620. However, in other embodiments, the slide tube 640 may not be coupled to the tubular body 620 in this manner. As further shown in FIG. 6C, the implant 104 can include an ejection tube 650 disposed in the outer elongate tubular body 620 such that the slide tube 640 can slide along the ejection tube 650. In one embodiment, the ejection tube 650 can be attached to the core pin 630.

Generally, the ejection tube 650 can include two portions, an implant portion 650i and a removable portion 650r. In an exemplary embodiment the ejection tube 650 is frangible at a separable break 654, which divides the distal implant portion 650i from the proximal removable portion 650r. The separable break 654 can be a weakened portion of the ejection tube 650, thereby allowing the ejection tube 650 to be frangible. Following deployment of the implant 104 in a tissue puncture, the ejection tube 650 can be broken into the two portions 650i and 650r and the removable portion 650r can be removed from the implant.

In some embodiments, a tether attachment (not shown) can be provided on the ejection tube 650 to allow a tether (also not shown) to be coupled to the implant 104. The tether can extend proximally from the implant 104 and can assist in locating the implant 104 at a desired location by acting as a tensioning member. The tether can be configured and used as described, for example, in U.S. Patent Application Publication No. 2013/0165963, entitled "Devices and Methods for Occluding or Promoting Fluid Flow," filed Dec. 21, 2011, the contents of which are incorporated herein by reference in their entirety.

In the illustrated embodiment, the guide wire 120 can be used to deploy the implant 104. Because the guide wire 120 is coupled to the implant 104, extends through the handle assembly 102, and is coupled to the body rear 110 so that the body rear 110 and the guide wire 120 move together, movements of the body rear 110 are transferred, through the guide wire 120, to the implant 104 to cause the proximal and distal wings thereof to deploy.

As shown in FIG. 6C, the guide wire 120 that can be slidably received within the guide tube 106 can be coupled distally to the ejection tube 650 at the distal end 120d of the guide wire 120. When the guide wire 120 is rotated and moved proximally, to follow the rotation and proximal movement of the body rear 110, at least one of the proximal and distal portions 620a, 620b can be rotated and compressed such that the proximal and distal wings 624a, 624b are formed, as discussed below.

The guide wire 120 can be manipulated so as to slide the core pin 630 toward the slide tube 640. In the illustrated embodiment, the core pin 630 is configured such that sliding the core pin 630 toward the slide tube 640 will cause a first force to be applied to the outer elongate tubular body 620 such that the body 620 moves a first distance in a proximal direction to expand and form the distal wings 624b. The core pin 630 is also configured such that sliding the core pin 630 further toward the slide tube 640 will cause a second force to be applied to the outer elongate tubular body 620 such that the body 620 moves a second distance in a proximal direction to expand and form the proximal wings 624a.

Figure 14A:
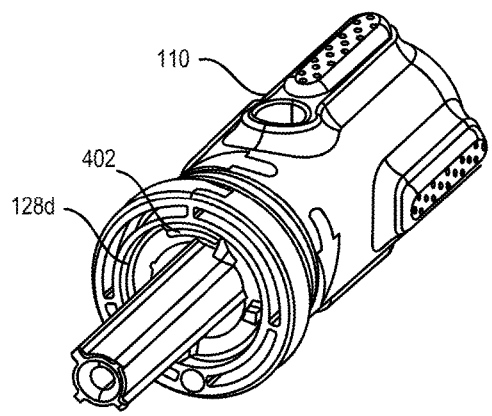
FIG. 14A is a perspective view of the handle assembly of FIG. 3, including a ring, in an initial position, prior to deployment of the first set of wings of the implant.

FIG. 5 illustrates the handle assembly 102 prior to deployment of the implant 104. As shown, the ring connector 128 is positioned such that it is coupled to the body front 108. The compression spring 142 applies force to the distal end of the inner shaft 126. The body rear 110 generally does not move in response to the force applied by the compression spring 142 as the body rear 110 is slidably engaged via the tab 402 (FIG. 4) with the ring connector 128, as shown in FIG. 14A. As mentioned above, the guide wire 120 is received through the guide tube 106. The guide tube 106 is attached to the body front 108 at a location 502 and it generally does not rotate during deployment of the implant 104.

In some embodiments, the guide wire 120 causes selective expansion and compression of the outer elongate tubular body 620 of the implant 104 and/or activation of the frangible portion of the ejection tube 650 (e.g., the break 654). For example, when the guide wire 120 is rotated and moved proximally, the tubular body 620 is caused to be axially rotated and compressed so that portions of the elongate tubular body 620 between the slits 622a, 622b extend outward away from a central axis B of the tubular body 620 to form the proximal and distal wings 624a, 624b.

To deploy an implant using an actuator described herein, a portion, such as a body rear, of the actuator is first rotated with respect to another portion, such as body front, thereof via a first rotation stroke in a first direction to deploy a first set of wings of the implant. As the body rear is rotated in the first direction, it moves a distance axially away from the body front to move the first set of wings into a deployed configuration. The body rear is then rotated via a second rotation stroke in a second, opposite direction to deploy a second set of wings of the implant. As the body rear is rotated in the second direction, it moves to a second distance, which is greater than the first distance, axially away from the body front to move the second set of wings into a deployed configuration. After the first and second sets of wings are deployed in this manner, the actuator can be manipulated (e.g., a lever coupled thereto is moved) so that the body rear again moves axially to a third distance, which is greater than the second distance.

Referring to FIGS. 7-14D, one embodiment of a method of actuating the actuator 100 to deploy an implant, such as implant 104, is described. The method includes manipulating the actuator 100 and/or or other suitable delivery assembly to deliver to and position the implant 104 at a surgical site. One skilled in the art will appreciate that the delivery assembly can include any suitable components, including those not shown herein, that can be configured to deliver the implant 104 to the surgical site and position the implant 104 in a ready-to-deploy configuration. The implant 104 can be positioned with respect to an opening in tissue to be sealed so that its mid-portion (e.g., portion 623 in FIG. 6A) spans the opening, and proximal and distal portions (e.g., portions 620a, 620b in FIG. 6A) are disposed on opposite sides of the opening. Each of the proximal and distal portions 620a, 620b can be rotated and compressed to form respective proximal and distal wings 624a, 624b.

In some embodiments, an implant, such as implant 104, can be used to close a body lumen, such as a fallopian tube. Wings are deployed within the body lumen to anchor the implant into the walls of the lumen thereby blocking the flow of fluids and any other substances through the lumen.

Figure 7:
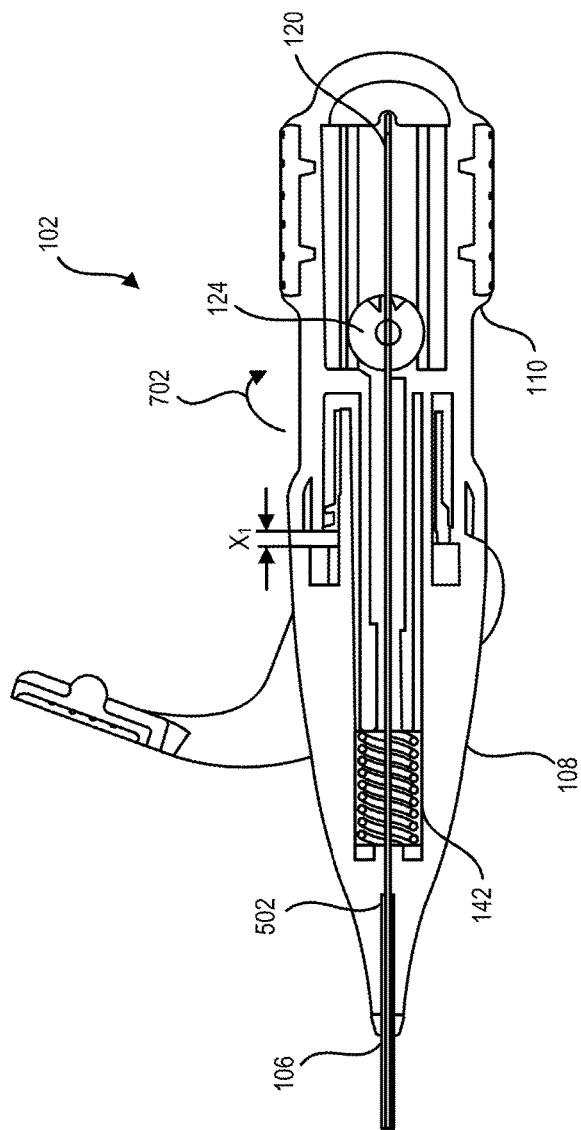
FIG. 7 is a side cross-sectional view of the handle assembly of FIG. 4 during deployment of a first set of wings of the implant.

In an exemplary embodiment, to deploy a first set of wings of the implant 104, such as distal wings 624b (FIG. 6C), the body rear 110 is rotated via a first rotation stroke in a first direction (e.g., clockwise) indicated by an arrow 702 in FIG. 7 about the longitudinal axis A of the handle assembly 102. The first direction can be conveniently indicated on the surface of the handle assembly 102, e.g., using the marking 114A shown in FIG. 2.

The ring connector 128 includes engaging features configured to engage with engaging feature(s), such as the body rear tab 402, formed on the ring connector 128. The engaging features of the ring connector 128 include one or more radial channels or slots formed around the outer surface of the ring connector 128 (within or on the surface) in communication with each other. The slots are formed around a circumference of the outer surface of the ring connector 128 so that they are shaped as an arc translating radially around the circumference of the ring connector 128. The slots communicate via openings extending longitudinally relative to the longitudinal axis A of the handle assembly 102. Such configuration allows the body rear tab 402 to move about the ring connector 128 for rotation, while also moving axially proximally from the body front 108. The engaging features of the ring connector 128 also include a longitudinal slot that receives therein the body rear tab 402 so that the body rear tab 402 moves further proximally within the longitudinal slot.

Figure 8A:
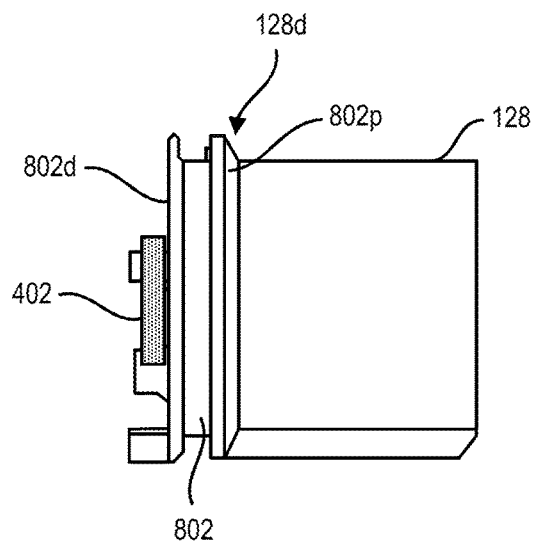
FIG. 8A is a side view of a ring connector and a body rear tab of the handle assembly of FIGS. 5 and 7 prior to deployment of the first set of wings of the implant.

In the beginning of the first rotation stroke, the body rear tab 402 abuts a more distal wall 802d of the walls 802d, 802p forming a first slot 802. The distal wall 802d can be a part of a distal edge or flange 128d of the ring connector 128. As the body rear 110 is rotated through the first rotation stroke, the body rear tab 402 slides in the first direction along the distal wall 802d, as shown in FIG. 8A. Such rotation can include a limited amount of axial movement or no axial movement can be associated with the rotation. This movement causes distal portion 620b of the elongate tubular body 620 of the implant 104 (FIGS. 6A-6C) to expand outwardly so that distal wings 624b of the implant 104 become partially deployed.

Figure 8B:
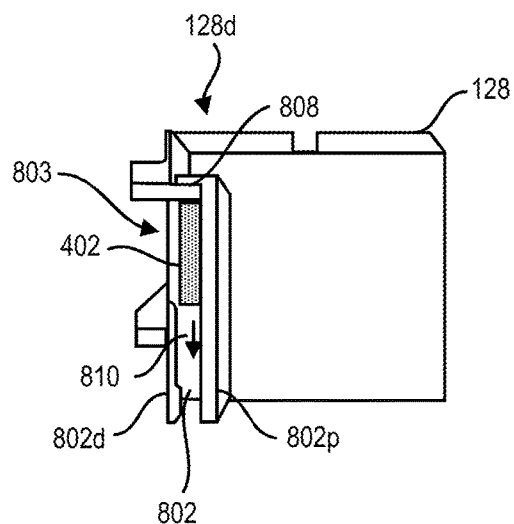
FIG. 8B is a side view of the ring connector and the body rear tab of FIG. 8A after deployment of the first set of wings.
Figure 14B:
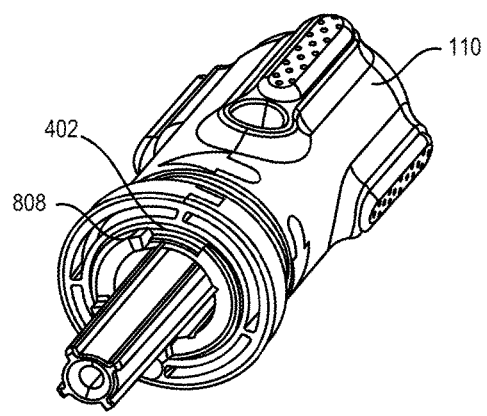
FIG. 14B is a perspective view of the handle assembly and the ring connector of FIG. 14A, in a second position, after deployment of the first set of wings.

At the end of the first rotation stroke, an opening 803 in the more distal wall 802d of the distal flange 128d of the ring connector 128 allows the body rear tab 402 to move axially in the proximal direction so that the body rear tab 402 becomes positioned against the recessed wall 802p in the ring connector 128. As a result of the biasing force applied by the compression spring 142, the body rear tab 402 is biased to slide along the wall of the first slot 802 and to move through the opening 803, causing the body rear tab 402 to be spaced proximally apart from its initial position before the start of the first rotation stroke. Such axial movement of the body rear tab 402 through the opening 803 causes the body rear 110 to slide axially away from the body front 108 by a distance X1, as shown in FIG. 7. As shown in FIG. 8B, once the body rear tab 402 moves through the opening 803, the body rear tab 402 abuts a stop surface 808 in the distal flange 128d that prevents further axial (proximal) and rotational movement of the body rear 402, as shown in FIGS. 8B and 14B. In this way, the first rotation stroke is complete and the body rear 110 is prevented from rotating beyond the first rotation stroke in the first direction.

As the body rear 110 moves proximally from the body front 108 by the distance X1 (FIG. 7), the guide wire 120 affixed to the body rear 110 also moves proximally by the same distance, which causes the distal portion 620b of the implant 104 to compress so that the distal wings 624b move to their final configuration as shown in FIG. 6C.

After the distal wings 624b are deployed, the handle assembly 102 is further manipulated to cause the proximal wings 624a to deploy. It should be appreciated that the distal wings 624b are shown to be deployed prior to the deployment of the proximal wings 624a by way of example only, as, in some embodiments, the proximal wings 624a can be deployed before the distal wings 624b are deployed, or the proximal and distal wings 624a, 624b can be deployed substantially simultaneously.

Figure 9:
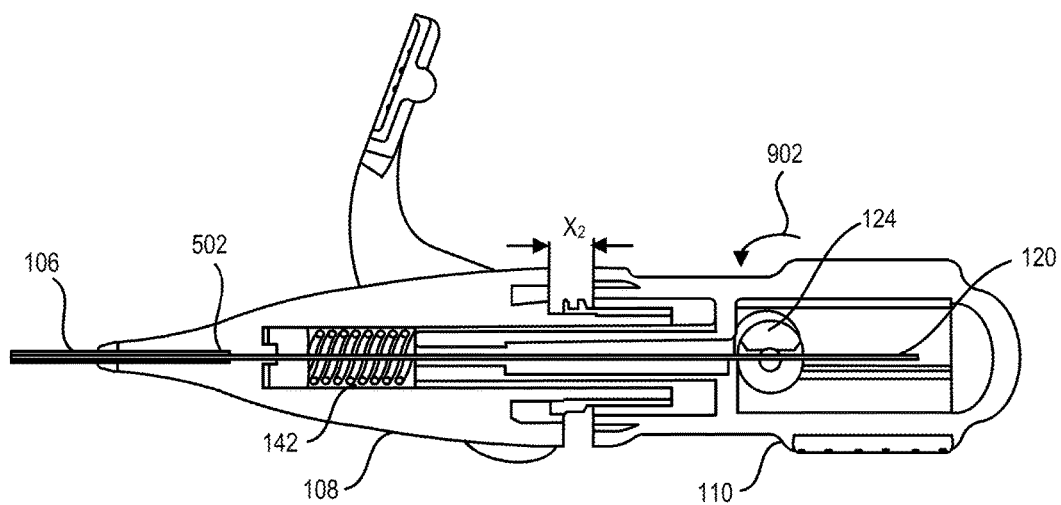
FIG. 9 is a side cross-sectional view of the handle assembly of FIG. 5 during deployment of a second set of wings of the implant.

In the exemplary embodiment, to deploy a second set of wings of the implant 104, such as proximal wings 624a (FIG. 6C), the body rear 110 is rotated via a second rotation stroke in a second direction (e.g., counterclockwise) indicated by an arrow 902 in FIG. 9 about the longitudinal axis A of the handle assembly 102. The second direction can be conveniently indicated on the surface of the handle assembly 102, e.g., using the marking 114b shown in FIG. 2.

When the body rear tab 402 is positioned at the end of the first rotation stroke against the stop surface 808, as shown in FIG. 8B, the body rear tab 402 is able to move in a second (e.g., counterclockwise) direction within the first slot 802. Thus, the body rear tab 402 is able to slide within the first slot 802 in the direction indicated by a directional arrow 810 in FIG. 8B. The rotation of the body rear 110 in the second direction causes proximal portion 620a of the elongate tubular body 620 of the implant 104 (FIGS. 6A-6C) to flare outwardly so that proximal wings 624a of the implant 104 become partially deployed.

Figure 10:
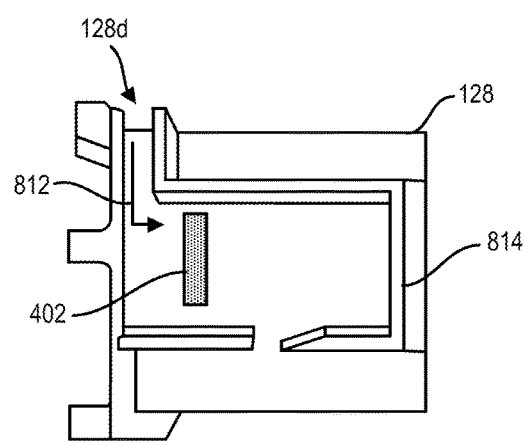
FIG. 10 is a side view of the ring connector and the body rear tab of FIG. 8B after deployment of the second set of wings.
Figure 14C:
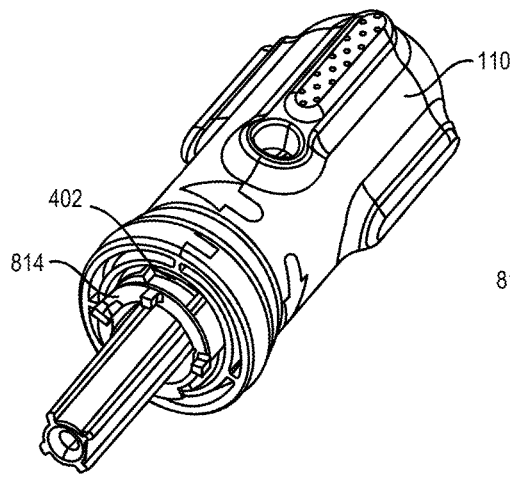
FIG. 14C is a perspective view of the handle assembly and the ring connector of FIG. 14B, in a third position, after deployment of the second set of wings.

While the body rear 110 is rotated via the second rotation stroke, the body rear tab 402 slides within the first slot 802 in the direction 810 until it is urged, due to the configuration of the first slot 802 and biasing force applied by the compression spring 142, to move into a second slot 814, as shown in FIGS. 10 and 14C. In this way, the body rear tab 402 becomes more axially spaced apart from the body front 108 by a distance X2, as shown in FIG. 9. This axial movement of the body rear 110 away from the body front 108 also causes the guide wire 120 to move proximally by the same distance, which, in turn, causes the proximal portion 620a of the implant 104 to compress so that the proximal wings 624a move into their final, fully deployed configuration.

Figure 14D:
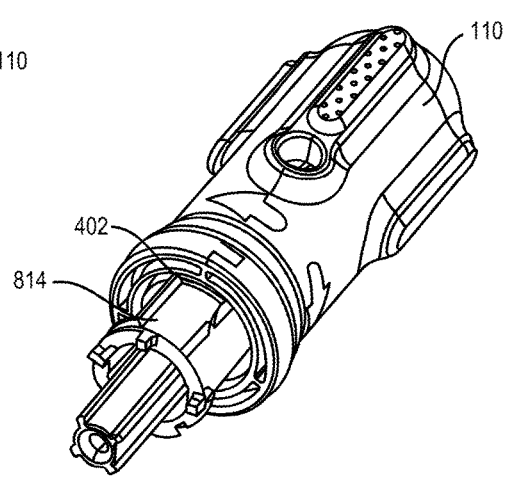
FIG. 14D is a perspective view of the handle assembly and the ring connector of FIG. 14C, in a fourth position, after the implant is ejected from the actuator.

As shown in FIGS. 10, 14C, and 14D, the second slot 814 is formed longitudinally along an outer surface of the ring connector 128 and it can extend through a portion or substantially the entire length of the ring connector 128. The second slot 814 has a suitable width so that it can receive the body rear tab 142 therein.

When the body rear tab 402 is positioned within the second slot 814 as shown in FIGS. 10 and 14C, the body rear 110 is thereby prevented from rotating beyond the second rotation stroke, and it is prevented from rotating in either the first or second direction.

Figure 11:
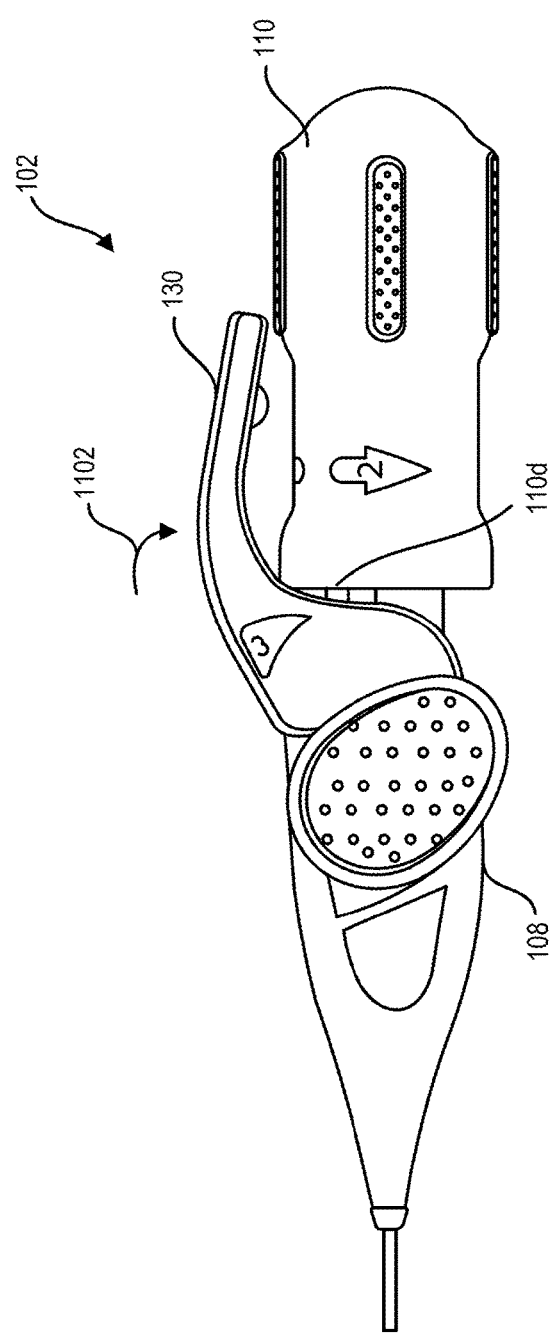
FIG. 11 is a side view of the handle assembly of FIG. 2 during ejection of the implant from the actuator.
Figure 12:
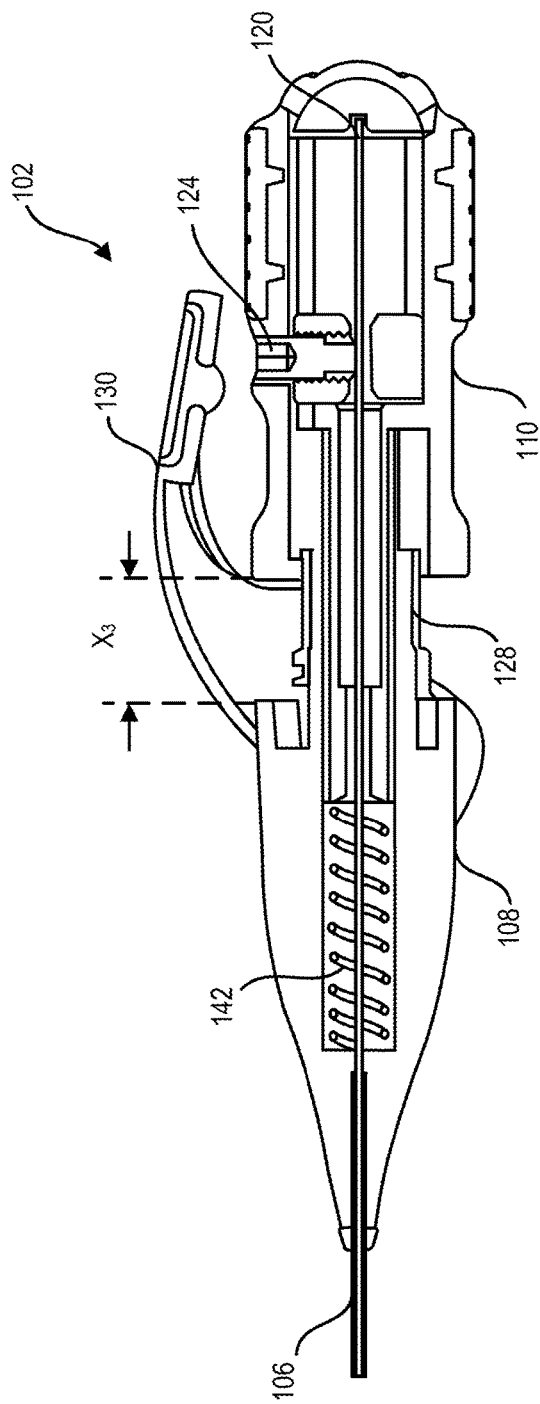
FIG. 12 is a side cross-sectional view of the handle assembly of FIG. 11.

After the proximal and distal wings 624a, 624b of the implant 104 are deployed, the implant 104 is ejected from the actuator 100 such that the implant 104 remains at the surgical site. In some embodiments, to eject the implant 104 from the actuator 100, the lever 130 coupled to the housing 101 is moved proximally in a direction shown by a directional arrow 1102 in FIG. 11. The lever 130 applies a compressive load to the distal end 110d of the body rear 110 so that the rotation of the lever 130, as shown in FIG. 11, causes the body rear 110 to further slide axially away from the body front 108 so that the body rear 110 is spaced axially apart from the body front 108 by a distance X3, as shown in FIG. 12.

Figure 13:
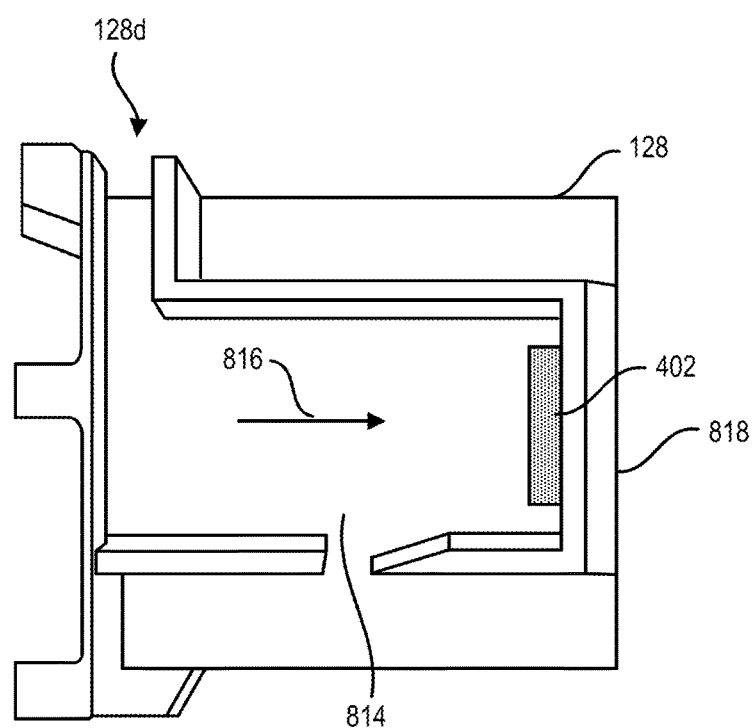
FIG. 13 is a side view of the ring connector and the body rear tab of FIG. 10 after the implant is ejected from the actuator device.

As shown in FIG. 13, as the lever 130 is being moved, the body rear tab 402, positioned in the second slot 814 of the ring connector 128 at the end of the second rotation stroke, slides within the second slot 814 in a direction as shown by a directional arrow 816. The amount of such movement of the body rear tab 402 is controlled by a longitudinal length of the second slot 814 and the distance that lever 130 travels as it is moved. The body rear tab 402 moves in this manner until it abuts a top surface or a proximal end 818 of the slot 814, as shown in FIGS. 13 and 14D. In this way, further axial movement of the body rear 110 away from the body front 108 is prevented.

As the body rear 110 slides axially away from the body front 108, the guide wire 120 attached to the body rear 110 also moves proximally. In one exemplary embodiment, the guide wire 120 is coupled at the distal end thereof to the ejection tube 650 of the implant 104 which, in turn, is coupled to the core pin 630. Thus, the tension applied to the guide wire 120 as a result of the force applied by the lever 130 to the body rear 110 causes the core pin 630 to move proximally against the distal tip of the slide tube 640. As the lever 130 is rotated through the end of its stroke, the increased tension on the guide wire 120 leads to an increased compression force between the core pin 630 and the slide tube 640 at a location indicated by a numerical reference 680 in FIG. 6C. When a force applied to guide wire 120 exceeds a certain threshold force, the ejection tube 650 attached at a proximal end thereof to the guide wire 120 can break into two portions, an implant portion 650i and a removable portion 650r, at the frangible location 654 shown in FIG. 6C. The implant portion 650i remains with the implant 104, whereas the removable portion 650r can be removed. The implant 104 can then be separated from the actuator 100.

As discussed above, the configuration of the ring connector 128 can control the manner in which the implant 104 is ejected from the actuator 100. Once the body rear tab 402 abuts the stop surface 818 in the second slot 814, the deployment of the implant 104 is complete and the actuator 100 can be removed from the surgical site. In this way, the implant 104 is ejected from at least a portion of the actuator 100 in a simple manner, with a single rotation of the lever 130.

FIGS. 15-19C illustrate another embodiment of an actuator 1500 configured to deploy an implant such as implant 104 shown in FIGS. 1 and 6A-6C. The actuator 1500 is configured similar to actuator 100 of FIGS. 1, 2-5 and 7-14D. However, the actuator 1500 additionally includes a biasing mechanism that urges a proximal portion (the body rear) of the actuator 1500 to slide axially away from a distal portion (body front) thereof when the body rear is rotated with respect to the body front. The biasing mechanism includes push tabs extending from a proximal end of the body front and variable-width slots axially formed in a distal end of the body rear and configured to engage with the push tabs. As the body rear is rotated to deploy a first portion of an implant, each push tab slides within a respective slot from a deeper-width end of the slot toward a shallow or zero-depth end thereof so that, when the push tab reaches the zero-depth end of the slot, the tab comes out of the slot and pushes the body rear proximally, away from the body front. Similar to actuator 100, the actuator 1500 includes a ring connector configured to control amount of rotational and axial movement of the body rear with respect to the body front during deployment and ejection of the implant. The ring connector can include engaging features, that are similar to those formed on ring connector 128 (FIGS. 3, 8A, 8B, 10, 13, and 14A-14D), and that are configured to engage a tab formed on the body rear.

Figure 15:
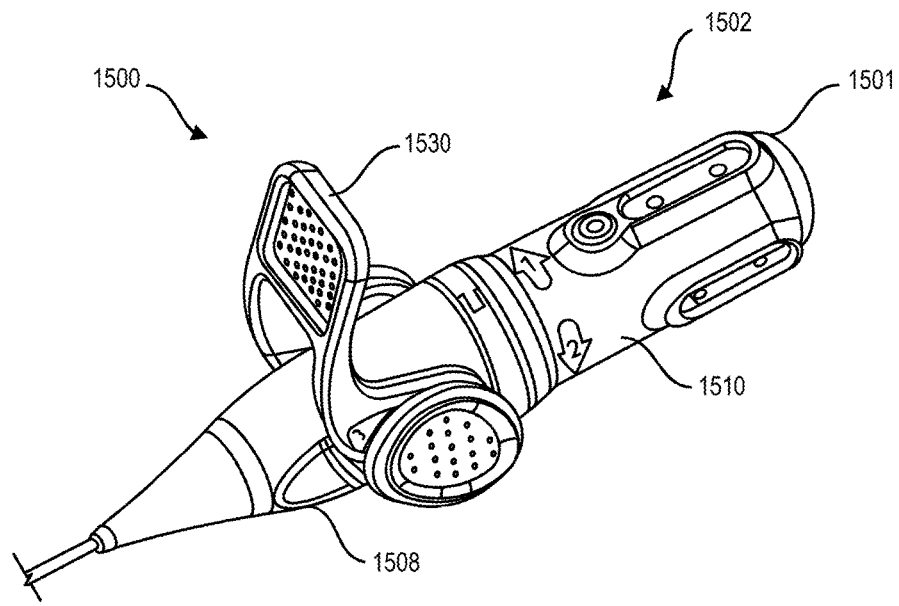
FIG. 15 is a perspective view of another exemplary embodiment of an actuator device.

As shown in FIG. 15, similar to actuator 100, the actuator 1500 includes a handle assembly 1502, including a housing 1501 having a distal portion or body front 1508 and a proximal portion or body rear 1510 configured to move axially with respect to the body front 1508. As shown in FIG. 15, the body front 1508 has a lever 1530 attached thereto which can be similar to lever 130 of the actuator 100. The actuator 1500 can have components similar to components of actuator 100, which are not shown in detail. It should be appreciated that the handle assembly 1502 and its components can have any suitable configurations, as described embodiments are not limited in this respect.

Figure 16:
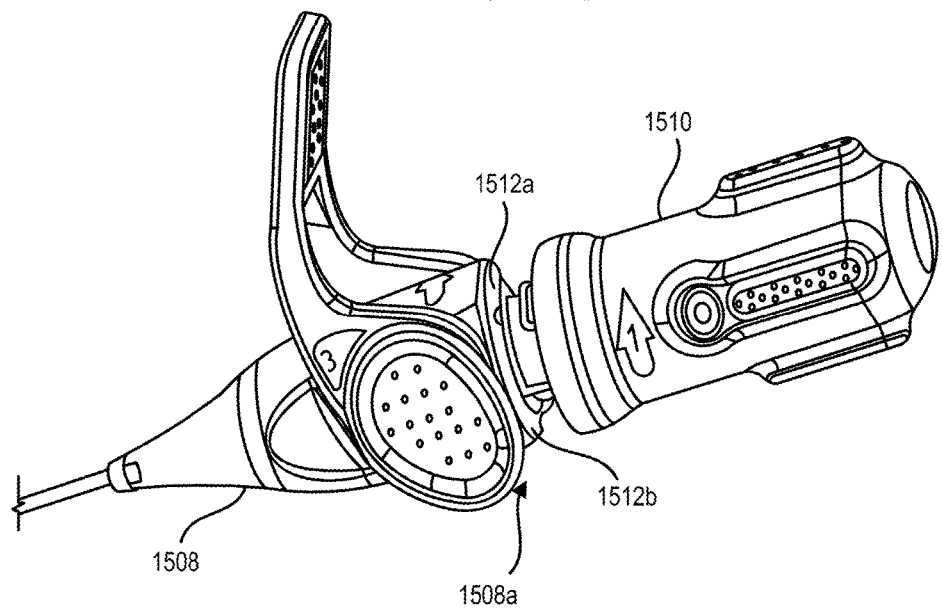
FIG. 16 is a perspective view of a handle assembly of the actuator of FIG. 15 following deployment of a second set of wings of an implant.
Figure 17:
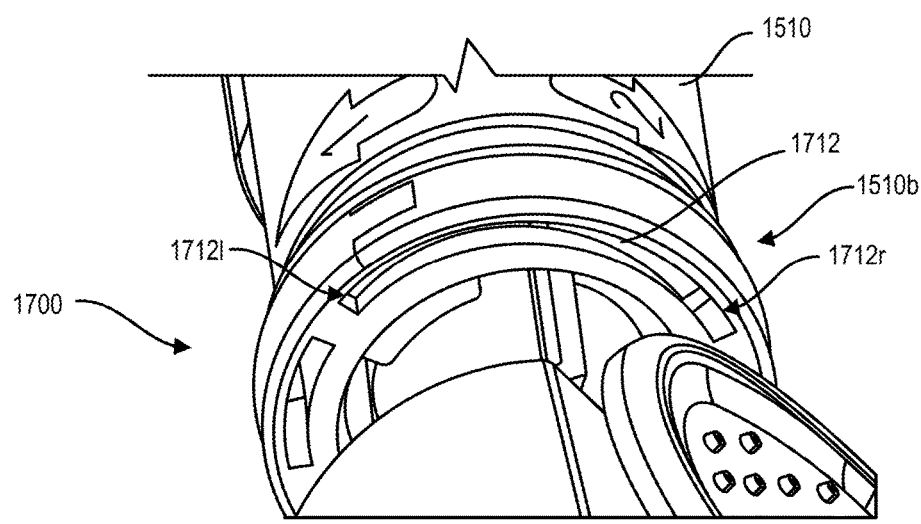
FIG. 17 is a perspective view of a slot formed in the body rear of the actuator of FIG. 15.

As mentioned above, the actuator 1500 includes push tabs 1512A, 1512B coupled to a proximal end 1508a of the body front 1508, as shown in FIG. 16, illustrating the actuator 1500 following deployment of a second set of wings of an implant. The actuator 1500 also includes slots 1712 formed in a distal end 1510b of the body rear 1510 (one slot 1712 is shown in FIG. 17) which are configured to engage with the push tabs 1512A, 1512B of the body front 1508.

As shown in FIG. 16, where the body rear 1510 is shown as moved proximally away from the body front 1508 following deployment of the second set of wings, the push tabs 1512A, 1512B extend from the body front 1508 to a certain height and they are disposed about 180° away from each other. The slots 1712 formed in the distal end 1510b of the body rear 1510 are also disposed about 180° away from each other so that each of the slots 1712 engages with a respective push tab 1512A, 1512B. FIG. 17 illustrates a slot 1712 that is configured to engage with, for example, the push tab 1512A. Another slot that is not shown herein can have the same or substantially the same geometry as the slot 1712. As shown in FIG. 17, the slot 1712 is formed within an inner wall of the distal end 1510b of the body rear 1510 so that the slot 1712 extends longitudinally within the inner wall. The slot 1712 can have a slightly convex general shape so that it curves inwards and it has an internal shape so that at least a portion of the slot 1712 can receive therein the push tab 1512A. The slot 1712 can have a depth that decreases from a first portion 1712l, having a depth approximately equal to the height of the push tab 1512A, to a second portion 1712r, having a depth approximately equal to zero. In one illustrative embodiment, the depth of the slot 1712 can be constant (e.g., can be approximately equal to the height of the push tab 1512A) for approximately a half of the length of the slot 1712. However, in other embodiments, the depth of the slot 1712 can change (e.g., decrease) gradually, or in any other manner.

The handle assembly 1502 can be operated similarly to handle assembly 102 of FIGS. 1-3. Thus, to deploy a first set of wings (e.g., distal wings) of an implant (e.g., implant 104 in FIGS. 1 and 6A-6C), the body rear 1510 can be rotated in a first direction (e.g., clockwise) with respect to the body front 1508 through a first rotation stroke. To deploy a second set of wings (e.g., proximal wings) of the implant, the body rear 1510 can be rotated in a second, opposite direction (e.g., counterclockwise) with respect to the body front 1508 through a second rotation stroke. Similar to handle assembly 102, the handle assembly 1502 can include a compression spring, such as compression spring 142 (FIGS. 3, 5, 7, 9, and 13), that applies a constant longitudinal force to the body rear 1510 so that the body rear 1510 is biased away from the body front 1508.

Further, similar to handle assembly 102, the handle assembly 1502 can have a guide wire (e.g., guide wire 120 in FIGS. 3 and 5) extending therethrough so that the guide wire (not shown) is attached to the body rear 1510 and the guide wire 120 rotates and/or moves axially as the body rear 1510 is rotated and/or moved axially. A distal end of guide wire 120 is coupled to the implant, and rotation and axial movements of the guide wire cause each of the distal and proximal portions of the implant to expand or flare outwardly and to then compress. In this way, distal wings of the implant become partially deployed and then move to their final, fully deployed configuration. In a similar manner, proximal wings of the implant become partially deployed and then move to their final, fully deployed configuration.

In the illustrated embodiment, the geometry of the slot 1712 allows the body rear 1510 to be pushed axially away from the body front 1508. In the initial position of the actuator 1500, prior to deploying the distal and proximal wings of the implant, the push tab 1512A formed on the body front 1508 engages with the slot 1712 so that the push tab 1512A sits within the first portion 1712l that is sized to fit the push tab 1512A substantially in its entirety. When the body rear 1510 is rotated in the first direction (e.g., clockwise) with respect to the body front 1508 through the first rotation stroke to deploy a first set of wings (e.g., the distal wings), the push tab 1512A slides within the slot 1712 from the first, deeper-depth portion 1712l to the second, smaller or zero-depth portion 1712r thereof. As the push tab 1512A approaches a zero-depth portion within the portion 1712r, the decreasing depth of the slot 1712 causes the push tab 1512A to come out from the slot 1712. As a result, the body rear 1510 is pushed axially away from the body front 1508.

As the body rear 1510 is rotated with respect to the body front 1508 so that the push tab 1512A travels approximately the first half of the length of the slot 1712, the guide wire 120, coupled to the body rear 110, also rotates by the same amount. In use, the distal end of the guide wire 120 is attached to a distal tip of the implant 104, whereas a proximal end of the implant 104 is held in a fixed position against the tip of the guide tube 106, as shown in FIG. 6G. Thus, as the guide wire 120 is moved with the body rear 1510, the first set of wings (e.g., distal wings 624a of the implant 104) can expand outwardly to become partially formed. As the body rear 1510 is rotated to its stop position at the end of the first rotation stroke, as discussed below, it is pushed away from the body front 1508 as the push tab 1512A moves within the slot 1712 towards the portion 1712r. This action results in the guide wire 120 moving axially while rotating. This causes the elongate tubular body 620 of the implant 104 to compress, which, in turn, causes the partially formed wings 624b to move into their final, fully deployed configuration.

Similar to ring connector 128 of handle assembly 102, a ring connector 1800 of the handle assembly 1502 controls rotation and axial movement of the body rear 1510 as the body rear 1510 rotates to deploy distal and proximal wings 624b, 624a of the implant 104. For example, engaging features formed on or within the ring connector 1800 engage with an engaging feature(s), such as a body rear tab 1514, formed on the distal end of the body rear 1510 so that the body rear 1510 is unable to rotate beyond the first rotation stroke after the distal wings are deployed and the body rear 1510 is unable to rotate beyond the second rotation stroke after the proximal wings are deployed. The body rear tab 1514, schematically shown in FIGS. 19A-19C, can be similar to body rear tab 402 in FIG. 4, or it can have any other configuration.

Figure 18:
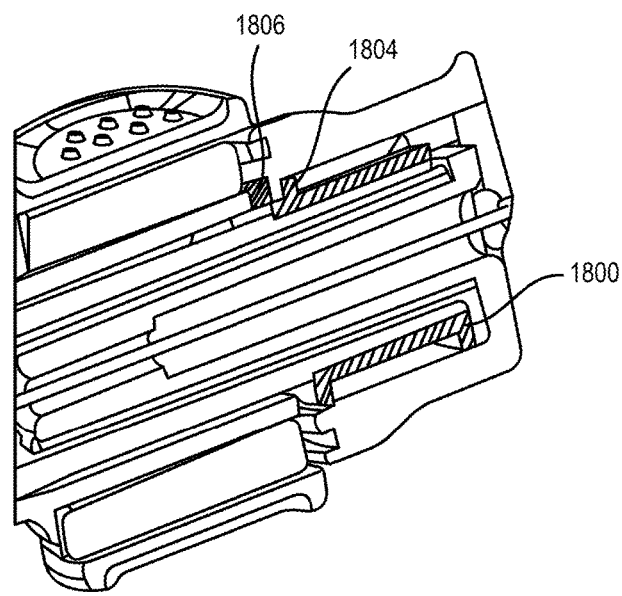
FIG. 18 is another perspective view of a slot formed in the body rear of the actuator of FIG. 15.
Figure 19A:
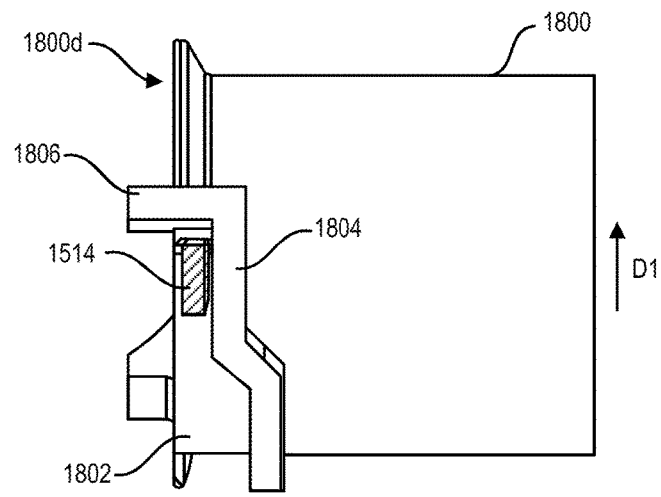
FIG. 19A is a side view of a ring connector and a body rear tab of the handle assembly of FIG. 15 following deployment of the first set of wings of the implant.

FIGS. 18 and 19A illustrate cross-sectional views of the handle assembly 1502 at the end of the first rotation stroke following deployment of the distal wings 624b. In the illustrated embodiment, while the body rear 1510 is rotated via the first rotation stroke in a direction D1 to deploy the distal wings 624b of the implant 104 as discussed above, the body rear tab 1514 slides against an outer edge of a distal end 1800d of the ring connector 1800 (e.g., within slot 1802) until it is positioned against a stop surface having an axial stop portion or wall 1804 and a rotational stop portion or wall 1806 formed on the ring connector 1800, as shown in FIGS. 18 and 19A. Once the body rear tab 1514 of the body rear 1510 abuts the axial and rotations stop walls 1804, 1806, the body rear 1510 is prevented from rotating beyond the first rotation stroke.

To deploy the second set of wings of the implant 104, such as proximal wings 624a, the body rear 1510 with the guide wire 120 attached thereto is rotated through a second rotation stroke in a second (e.g., counterclockwise) direction D2 (FIG. 19B) that is opposite to the first direction D1. After the distal wings 624b are deployed and the body rear tab 1514 abuts the axial and rotation stop walls 1804, 1806 as shown in FIG. 19A, the body rear tab 1514 is able to be rotated in the second direction D2, away from the axial and rotation stop walls 1804, 1806. The slot 1802, formed on the outer distal edge 1800d of the ring connector 1800, can extend radially around an entire circumference or a portion thereof of the outer surface of the ring connector 1800. The slot 1802 is configured and sized to slidably receive the body rear tab 1514 therein.

Figure 19B:
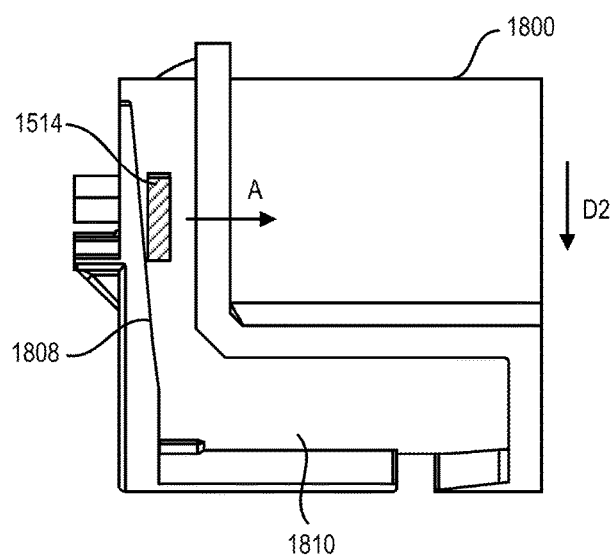
FIG. 19B is a side view of a ring connector and a body rear tab of the handle assembly of FIG. 19A during deployment of the second set of wings of the implant.

The configuration of the ring connector 1800 allows the body rear tab 1514 to move within the slot 1802 during the second rotation stroke until the body rear tab 1514 encounters an angular wall 1808 circumferentially formed on at least a portion of the outer surface of the ring connector 1800, as shown in FIG. 19B. The angular wall 1808, which can be formed as a continuation of one of the walls forming the slot 1802, is spaced proximally apart from the outer distal end of the ring connector 1800 and is angled proximally, so that, as the body rear tab 1514 slides against the angular wall 1808, the body rear tab 1514 moves proximally from the body front 1508.

In the illustrated embodiment, the engaging features of the ring connector 1800, such as the slot 1802, the angular wall 1808, and any other features that can be formed, are configured so that, as the body rear 1510 is rotated in the second direction, the body rear tab 1514 rotates to a certain distance while allowing axial movement of the body rear 1510 only to a short distance (e.g., from about 1 mm to about 3 mm), or preventing axial movement of the body rear 1510. During this movement, proximal portion 620a of the implant is rotated to cause the proximal wings 624a to extend outwardly to become partially formed. Following this partial deployment of the proximal wings 624a, the body rear tab 1514 abuts the angular wall 1808 of the ring connector 1800, as shown in FIG. 19B.

Figure 19C:
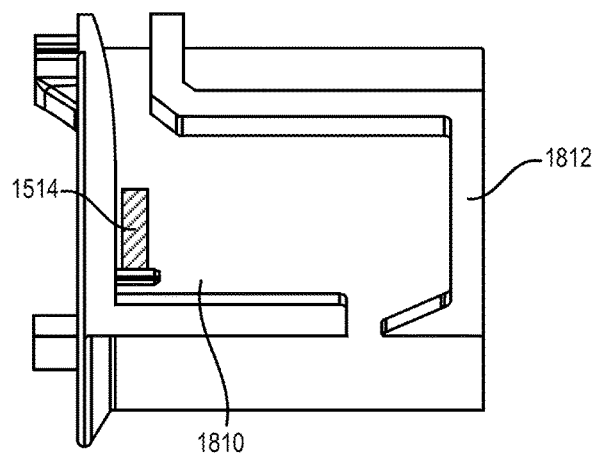
FIG. 19C is a side view of a ring connector and a body rear tab of the handle assembly of FIG. 19B following deployment of the second set of wings of the implant.

As the body rear 1510 is further rotated during the second rotation stroke along the angular wall 1808 as shown in FIG. 19B, the body rear tab 1514 is forced to move in a direction A (indicated in FIG. 19B). Because the angular wall 1808 angles proximally at a gradually increasing angle, as shown in FIG. 19B, the body rear tab 1514 rotates and moves further axially from the body front 1510. In this way, the body rear tab 1514 is caused to enter a longitudinal slot 1810 formed on the surface of the body rear 1510 along a longitudinal axis thereof, as shown in FIG. 19C. Such movement of the body rear 1510 causes the guide wire 120 attached thereto to move in the same manner (proximally), which thus causes the partially formed proximal wings 624a to move to their final, fully deployed configuration.

Figure 19D:
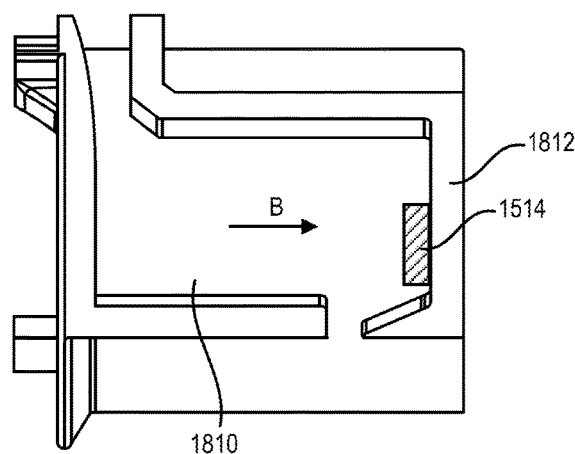
FIG. 19D is a side view of a ring connector and a body rear tab of the handle assembly of FIG. 19C following ejection of the implant.

After the proximal and distal wings 624a, 624b of the implant 104 are deployed, the implant 104 is ejected from the actuator 1500. To eject the implant 104, the lever 1530 is rotated towards the body rear 1510 to apply force thereto, which causes the body rear tab 1514 to move proximally within the slot 1810 in a direction B shown in FIG. 19D. As the force applied to the body rear 1510 and the guide wire 120 attached thereto in the direction B is increased, a frangible portion of the ejection tube 650 (e.g., at the separable break 654 shown in FIG. 6C) breaks, causing the implant 104 to separate from the actuator 1500. FIG. 19D illustrates the position of the body rear tab 1514 with respect to the ring connector 1800 following ejection of the implant 104. As shown in FIG. 19D, the body rear tab 1514 abuts a wall 1812 at a proximal end of the slot 1810, which can be disposed at a proximal end of the ring connector 1800. In this way, the body rear 1510 is prevented from any further movement in the direction B.

FIGS. 20-33 illustrate another exemplary embodiment of an actuator 2100 having a handle assembly 2102 for deploying an implant or closure device 2104. In this embodiment, an additional feature, such as a guide pin coupled to a distal portion or body front of the handle assembly 2102 can be used to control movement of a proximal portion or body rear with respect to the body front.

Figure 20:
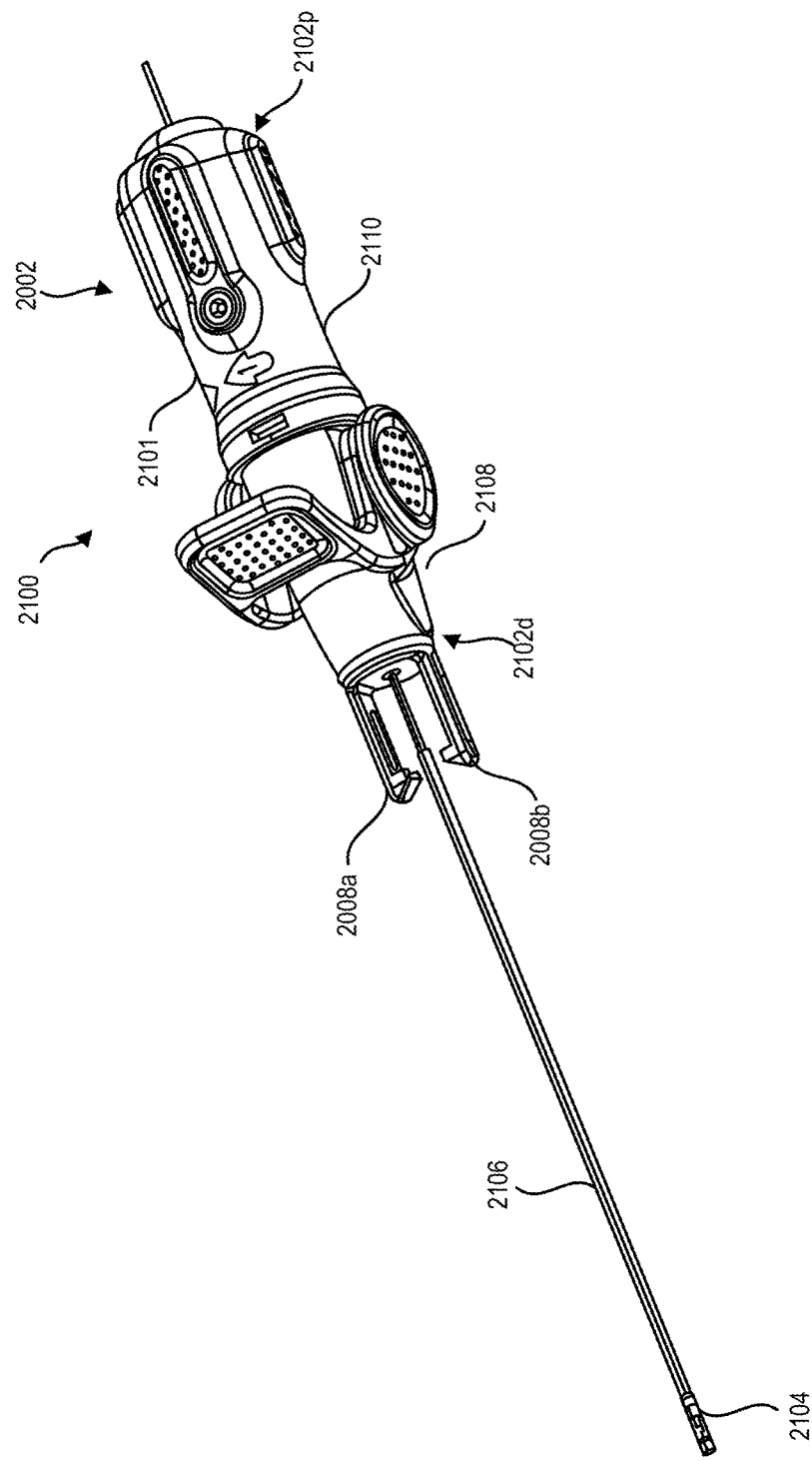
FIG. 20 is a perspective view of another exemplary embodiment of an actuator device having an implant disposed on a distal end thereof.
Figure 21:
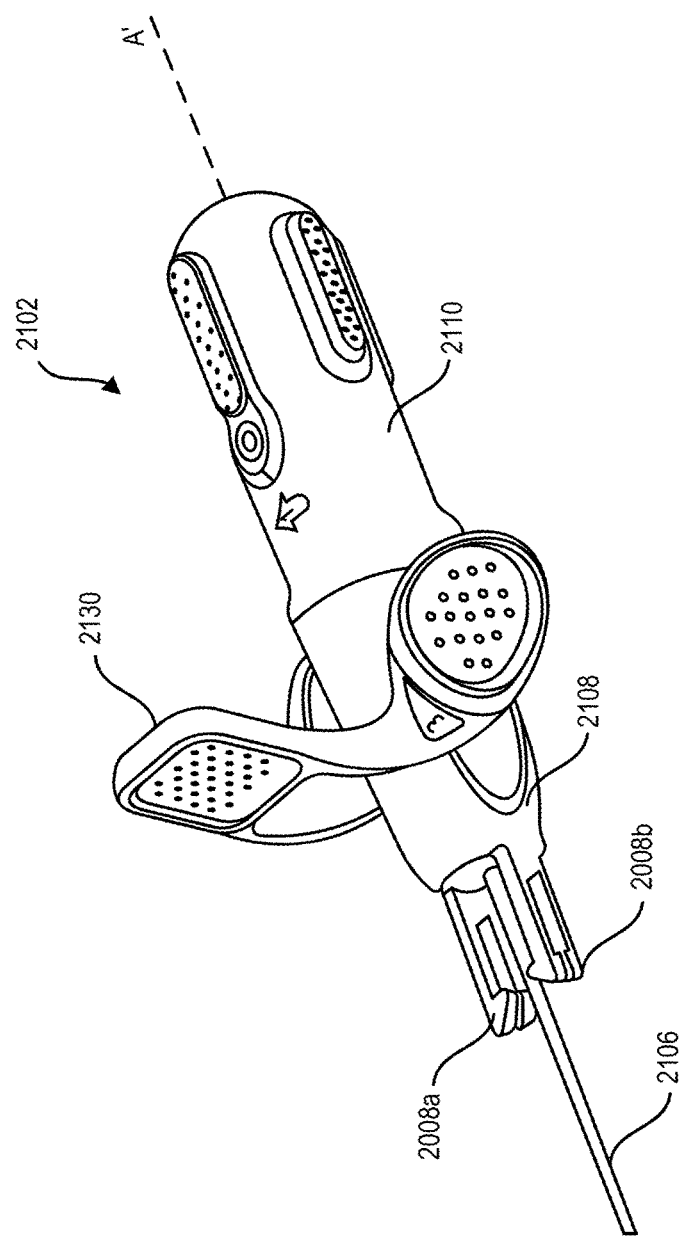
FIG. 21 is perspective view of a handle assembly of the actuator of FIG. 20.

The implant 2104 can be any suitable closure device for closing a tissue puncture. In some embodiments, the implant 2104 can be similar to the implant 104 shown in FIGS. 1 and 6A-6G. The handle assembly 2102 can be generally similar to handle assembly 102 of the actuator 100. Thus, as shown in FIGS. 20 and 21, the handle assembly 2102 is generally cylindrical and it can have a distally tapered distal end 2102d. As shown in FIG. 20, a distal end 2102d of the handle assembly 2102 is coupled to the implant 2104 via an elongate guide tube 2106.

As shown in FIGS. 20 and 21, the handle assembly 2102 includes a housing 2101 having a distal portion or body front 2108 and a proximal portion or body rear 2110 coupled to the body front 2108. Similar to body rear 110 or body rear 1510, the body rear or actuator portion 2110 is rotatable relative to the body front 2108 about a longitudinal axis A of the housing 2101 extending through the proximal and distal portions 2110, 2108.

As further shown in FIGS. 20 and 21, the handle assembly 2102 has locking tabs 2008a, 2008b extending distally from the distal end thereof. In some embodiments, the locking tabs 2008a, 2008b can be configured to engage with a suitable component (e.g., a valve or any other component) of an introducer sheath to securely attach the introducer sheath to the actuator 2100. The introducer sheath can be advanced (e.g., over a guidewire) toward a surgical site and can facilitate introduction of various devices to the surgical site.

Figure 22:
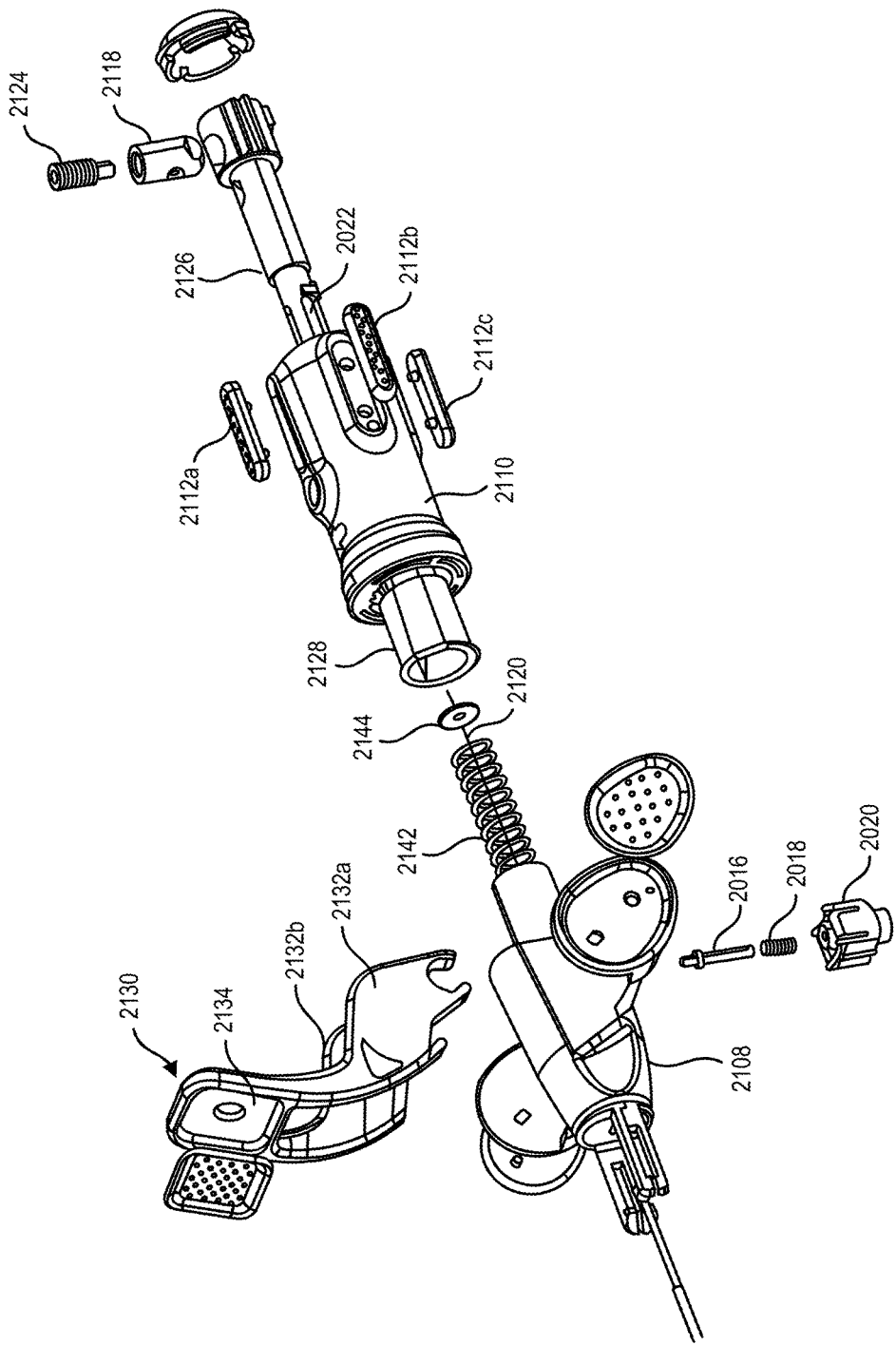
FIG. 22 is an exploded view of the handle assembly of the actuator of FIG. 21.

The body rear 2110 can have a variety of configurations. In the illustrated exemplary embodiment, as shown in FIG. 22, the body rear 2110 has a generally cylindrical shape and includes components that are similar to those included in the body rear 110 of the actuator 100. Thus, as shown in FIG. 22, the body rear 2110 includes gripping portions 2112a-d (only gripping portions 2112a-c are visible), a threaded insert 2118 configured to engage with a lock screw 2124 for attaching a guide wire 2120 to the body rear 2110, an inner shaft or actuator base 2126, and a body front ring or ring connector 2128 configured to be advanced over the actuator base 2126.

The body rear 2110 is shown in more detail in FIGS. 23 and 24, illustrating a lumen 2010 within the body rear 2110 as viewed from its distal end 2110d. FIGS. 23 and 24 show that the body rear 2110 includes a body rear tab 2402 formed in the lumen 2010 at the distal end of the body rear 2110 so that it extends toward the center of the lumen. As shown in FIG. 24, the inner wall of the lumen 2010 has tracks 2012 formed thereon configured to slidably receive therein the ring connector 2128. One skilled in the art will appreciate that any number of tracks or other retaining features having any suitable configuration can be formed, as embodiments are not limited in this respect.

Figure 26:
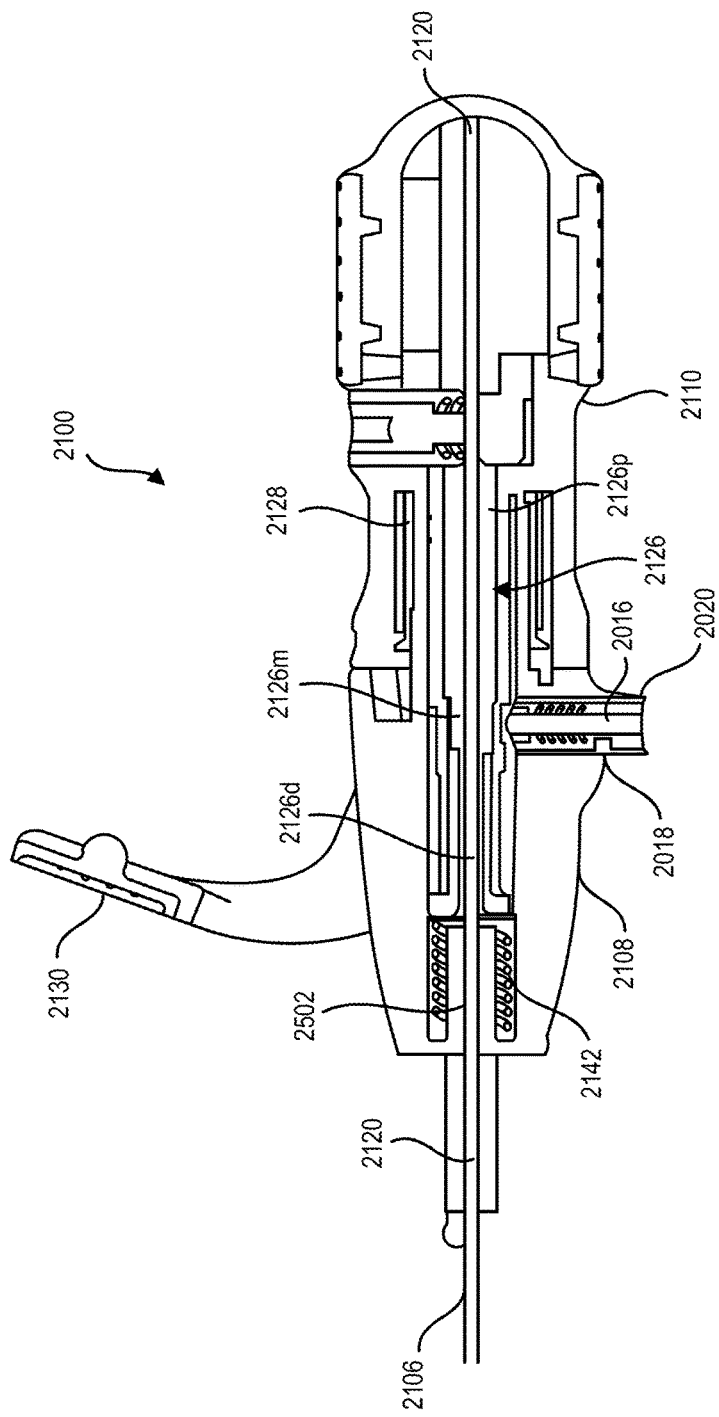
FIG. 26 is a side cross-sectional view of the handle assembly of FIG. 22 prior to deployment of wings of the implant associated therewith.

The ring connector 2128 receives therein an inner shaft or actuator base 2126 coupled in a suitable manner to the body rear 2110 and that has guide tracks 2022 formed therein along a longitudinal axis thereof. As shown in FIG. 26 illustrating the actuator 2100 prior to deployment of the implant 2104, the actuator base 2126 can have proximal portion 2126p, mid-portion 2126m, and distal portion 2126d, and it extends through both the body rear and front 2110, 2108. As shown, the proximal portion 2126p extends substantially through the body rear 2110 and the ring connector 2128, and the mid-portion 2126m is disposed distal to the proximal portion 2126p and having the guide tracks 2022 formed therein. In one illustrated embodiment, four guide tracks 2022 can be formed in the actuator base 2126. However, it should be appreciated that any suitable number of tracks can be formed.

As shown in FIG. 26, a distal end of the distal portion 2126d of the actuator base 2126 abuts a compression spring 2142 disposed in the body front 2108 so that the compression spring 2142 applies a constant force to the body rear 2110 by applying that force to the actuator base 2126.

The body rear 2110 can include any other suitable features. For example, as shown in FIGS. 23 and 24, the distal end 2110d can include axial slots 2014 that can engage with complementary components (e.g., prongs, tab or other protrusions) formed on a proximal end of the body front 2108 to facilitate engagement of the body rear 2110 with the body front 2108.

As shown in FIG. 26, the body rear 2110 receives therein the ring connector 2128 that can be coupled to the body front 2108. As shown in FIG. 25, the ring connector 2128 has a generally cylindrical tubular body with an outer flange 2128d extending radially from the outer distal edge thereof. Similar to ring connector 128 (FIGS. 3, 8A, 8B, 10, 13, and 14A-14D) and ring connector 1800 (FIGS. 18 and 19A-19D), the ring connector 2128 includes engaging features formed thereon that are configured to engage with the body rear tab 2402 of the body rear 2110 so that to control amount of rotational and axial movement of the body rear with respect to the body front during deployment and ejection of the implant. For example, the outer flange 2128d has an extension 2024 formed thereon that prevents the body rear tab 2402 from being rotated beyond the extension 2024, as discussed in more detail below. Further, the ring connector 2128 includes an opening 2028, also discussed in more detail below, that can receive therein the body rear tab 2402.

A person skilled in the art will appreciate that the ring connector 2128 can include any suitable features that permit rotation of the body rear 2110 with respect to the body front 2108 so that a first rotation stroke in a first direction to deploy a first set of wings of the implant has only a limited degree of rotation. Following the first rotation stroke, further rotation of the body rear 2110 is only permitted for a second rotation stroke, which is in a second, opposite direction. The ring connector 2128 also includes suitable features that likewise limit the amount of rotation for the second rotation stroke to deploy a second set of wings of the implant. The features formed in or on the ring connector 2128 also prevent the body rear 2110 from being rotated in either the first or the second directions after the first and second wings of the implant are deployed and they allow the implant to be ejected from the actuator.

The body front 2108 can also have a variety of configurations. In the illustrated exemplary embodiment, as shown in FIG. 22, the body front 2108 includes a compression spring 2142, a washer 2144, and a lever 2130 including arms 2132a, 2132b, and a middle portions 2134 disposed between the upper portions of the arms 2132a, 2132b. As further shown in FIG. 22, the body front 2108 includes a guide pin or pin member 2016 extending upward from the bottom thereof and configured to engage with the actuator base 2126 as discussed in more detail below. The guide pin 2016 is biased into engagement with the actuator base 2126 using a guide pin spring 2018 that can be advanced over it and the guide pin 2016 is attached to the body front 2108 using a cap 2020 shown in FIGS. 22 and 26. The guide pin spring 2018 pushes the guide pin 2016 (e.g., upwards) into engagement with the actuator base 2126 as discussed in more detail below.

As shown in FIG. 26, the guide wire 2120 extends through a guide tube 2106, the body front 2108, and the body rear 2110. The guide wire 2120 extends through body rear 2110 so that is does not protrude beyond the proximal end of the body rear 2110. The guide wire 2120 can be fixedly coupled to the body rear 2110 such that movement (e.g., rotation and/or axial movement) of the body rear 2110 causes the guide wire 2120 to also move in the same manner. In the example illustrated, the guide wire 2120 is attached to the body rear 2110 using the lock screw 2124 as shown in FIG. 26. However, it should be appreciated that any suitable locking mechanism, which can be disposed on the body rear 2110 in any manner, can be used to fixedly couple the guide wire 2120 to the body rear 2110.

Similar to guide wire 120 (FIGS. 1, 3, 5, 6C, 7, and 9), the guide wire 2120 extend through the guide tube 2106 such that the guide wire 2120 is coupled to the implant 2104 at a distal end thereof and can be used in deployment of the implant 2104. For example, as the guide wire 2120 rotates in a first direction and/or moves axially, a first (e.g., distal) portion of the implant 2104 is caused to expand outwardly to cause first (e.g., distal) wings to become partially deployed, and the first portion is then caused to compress so that the first wings move to a fully deployed configuration. In a similar manner, as the guide wire 2120 rotates in a second opposite direction and/or moves axially, a second (e.g., proximal) portion of the implant 2104 is caused to expand outwardly to cause second (e.g., proximal) wings to become partially deployed, and the second portion is then caused to compress so that the second wings move to a fully deployed configuration.

Figure 27:
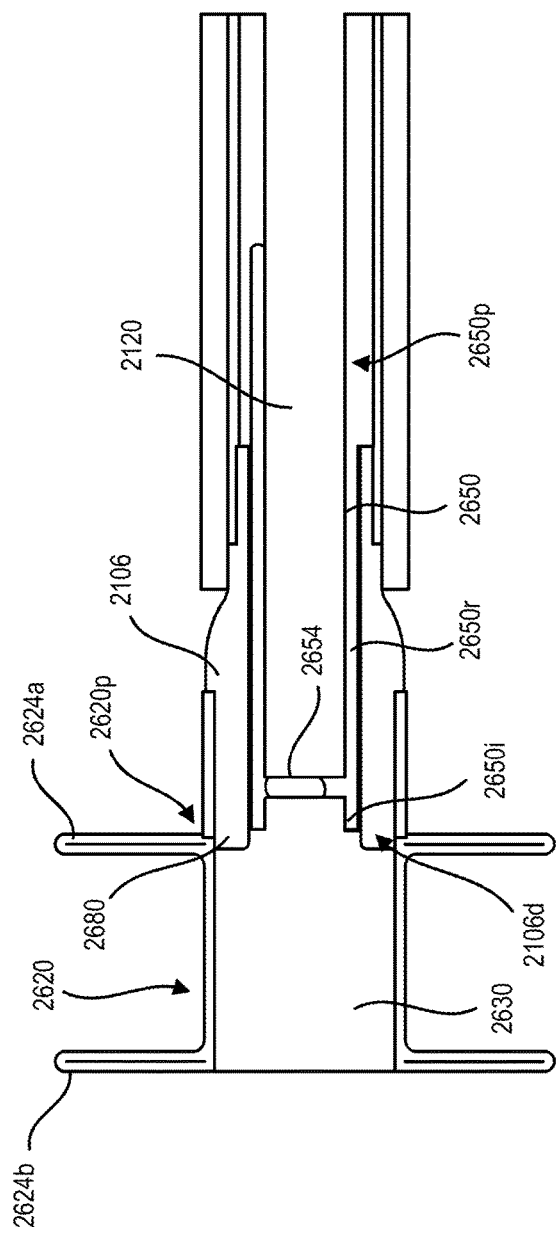
FIG. 27 is a side cross-sectional view of the implant of FIG. 20 after deployment of two sets of wings thereof and prior to ejection thereof from the actuator.

FIG. 27 illustrates one exemplary embodiment of the implant 2104 that can be deployed using the actuator 2100. The implant 2104 is generally similar to implant 104 shown in FIGS. 1 and 6A-6C, and not all features of the implant 2104 are shown in FIG. 27. Thus, the implant 2104 includes an outer elongate tubular body 2620 having proximal and distal portions configured to expand to form proximal and distal wings 2624a, 2624b that are shown in a deployed configuration in FIG. 27. As shown, a proximal end 2620p of the elongate tubular body 2620 is coupled to a guide tube 2106 receiving therein the guide wire 2120.

The implant 2104 can further include an ejection tube 2650 positioned within the outer elongate tubular body 2620. The ejection tube 2650 can include two portions, a distal implant portion 2650i and a removable proximal portion 2650r. The ejection tube 2650 can be frangible at a separable break 2654. Thus, when the implant 2104 is ejected from the actuator 2100, the ejection tube 2650 is separated into the portions 2650i, 2650r so that the distal implant portion 2650i remains with the implant 2104 and the proximal removable portion 2650r is removed.

As shown in FIG. 27, the proximal end 2650p of the ejection tube 2650 is coupled to the guide wire 2120 that is be slidably received within the guide tube 2106.

It should be appreciated that the implant 2104 can include any other suitable components that are not shown in FIG. 27 for the sake of complicity. For example, the implant 2104 can include a slide tube (e.g., slide tube 640 in FIG. 6C), a distal tip or guide tip (e.g., guide tip 670 in FIGS. 6A-6C) that facilitates advancement of the implant 2104, and any other suitable components.

Referring back to FIG. 26, the ring connector 2128 is positioned substantially within the body rear 2110 such that the ring connector 2128 is coupled to the body front 108. The compression spring 2142 applies constant force to the distal end of the actuator base 2126 attached to the body rear 2110. Prior to operation of the handle assembly 2102 to deploy the implant 2104, the body rear 2110 generally does not move responsive to the force applied by the compression spring 2142 since the body rear 2110 is engaged via the body rear tab 2402 with the ring connector 2128 as discussed below in connection with FIGS. 28 and 29.

The guide tube 2106 can be attached to the body front 2108 in a suitable manner, e.g., in a location 2502 shown in FIG. 26, so that the guide tube 2106 generally does not rotate during deployment of the implant 2104. The guide wire 2120 can be slidably received within the guide tube 2106 and a distal end of the guide wire 2120 can be coupled to a distal end of the implant 2104 via the ejection tube 2650. The guide wire 2120 selectively expands and compresses the outer elongate tubular body 2620 of the implant 2104 and/or activates the frangible portion (e.g., the break 2654) of the ejection tube 2650. For example, when the guide wire 2120 is rotated and moved proximally due to the movement of the body rear 2110, the elongate tubular body 2620 of the implant 2104 is caused to be rotated and/or compressed so that the proximal and distal portions of the elongate tubular body 2620 form the proximal and distal wings 2624a, 2624b to engage tissue therebetween.

Figure 28:
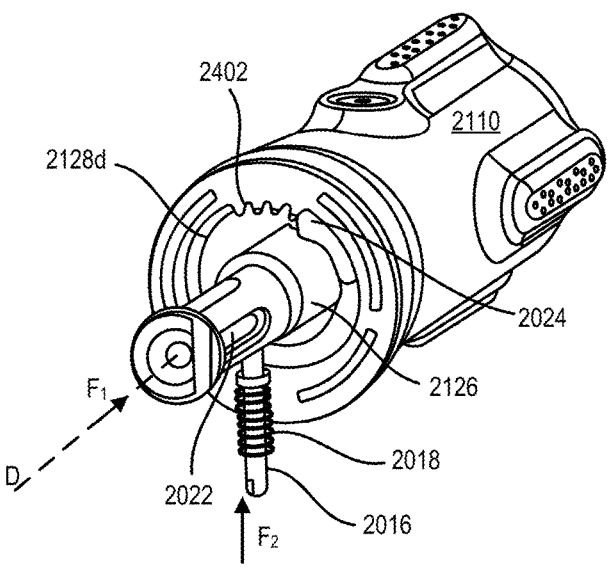
FIG. 28 is a perspective view of a body rear of a housing of the handle assembly of FIG. 26.
Figure 29:
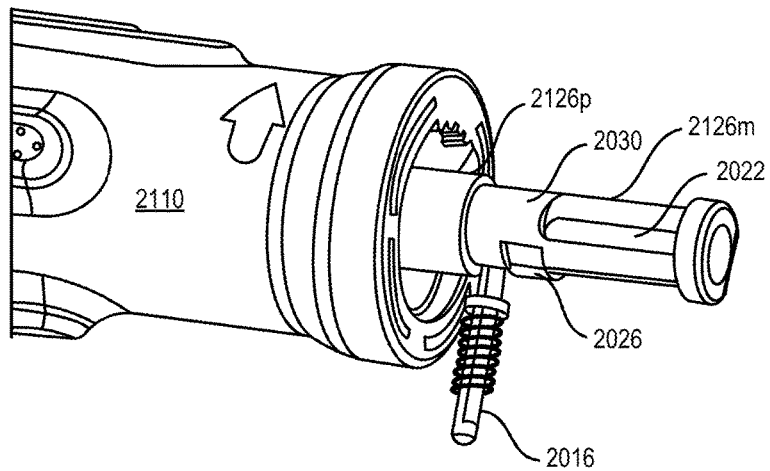
FIG. 29 is another perspective view of a body rear of a housing of the handle assembly of FIG. 26.

FIGS. 28 and 29 illustrate a position of the body rear 2110 prior to deployment of the implant 2104 in which the body rear 2110 engages with the ring connector 2128 via the body rear tab 2402. The ring connector 2128, which is attached to the body front 2108, can be disposed substantially within the body rear 2110 so that only the outer flange 2128d formed on a distal end of the ring connector 2128 is visible in FIG. 28. The actuator base 2146 attached to the body rear 2110 is disposed within the ring connector 2128 and protrudes distally from the body rear 2110 and the ring connector 2128. As shown in FIGS. 28 and 29, in this initial position, the body rear tab 2402 of the body rear 2110 abuts the outer flange 2128d of the ring connector 2128 so that the body rear tab 2402 sits against an extension 2024 formed on the outer flange 2128d.

As shown in FIGS. 28 and 29, the actuator base 2126 has guide tracks 2022 formed in its mid-portion 2126m along a longitudinal axis thereof. The guide tracks 2022 are formed in the surface of the mid-portion 2126m so that they are offset from a proximal end of the mid-portion 2126m that is free from the guide tracks. As shown in FIG. 29, the proximal end of the mid-portion 2126m of the actuator base 2126 has a corner protrusion 2026 formed thereon. Further, as schematically shown in FIG. 29, the proximal end of the mid-portion 2126m has a ramp 2030 circumferentially formed around the surface thereof, with a gradually increasing height that helps the guide pin 2016 to advance over the corner protrusion 2026, as discussed in more detail below.

The compression spring 2142 (shown in FIGS. 22 and 26) exerts a force F1 to the actuator base 2146, as schematically shown in FIG. 28. Because the body rear tab 2402 abuts the outer flange 2128d of the ring connector 2128, the body rear 2110 generally cannot move in the direction of the force F1 applied by the compression spring 2142.

The guide pin 2016 is affixed to the body front 2108 as shown in FIG. 26 such that it is oriented transverse (e.g., perpendicular) to the longitudinal axis of the body front 2108. The guide pin 2016 remains fixed while the body rear 2110 and the actuator base 2126, which extends therethrough, rotate during deployment of the implant 2104. In the position of the body rear 2110 shown in FIGS. 28 and 29, the force F2 from the guide pin spring 2018 pushes the guide pin 2016 against the cylindrical surface of the mid-portion 2126m of the actuator base 2126. As shown in FIGS. 28 and 29, prior to deployment of the implant 2104, the guide pin 2016 is not engaged with the tracks 2022 in the actuator base 2126 and it is disposed proximally of the corner protrusion 2026 disposed on the actuator base 2126.

In the position of the body rear 2110 shown in FIGS. 28 and 29, the body rear 2110 and the actuator base 2126 attached thereto rotate in a first direction (e.g., clockwise) allowing the body rear tab 2402 to slide along the outer flange 2128d of the ring connector 2128. In this initial position, the body rear 2110 is not able to rotate in a second (e.g., counterclockwise) direction, because the body rear tab 2402 sits against an extension 2024 formed on the outer flange 2128d.

Figure 30:
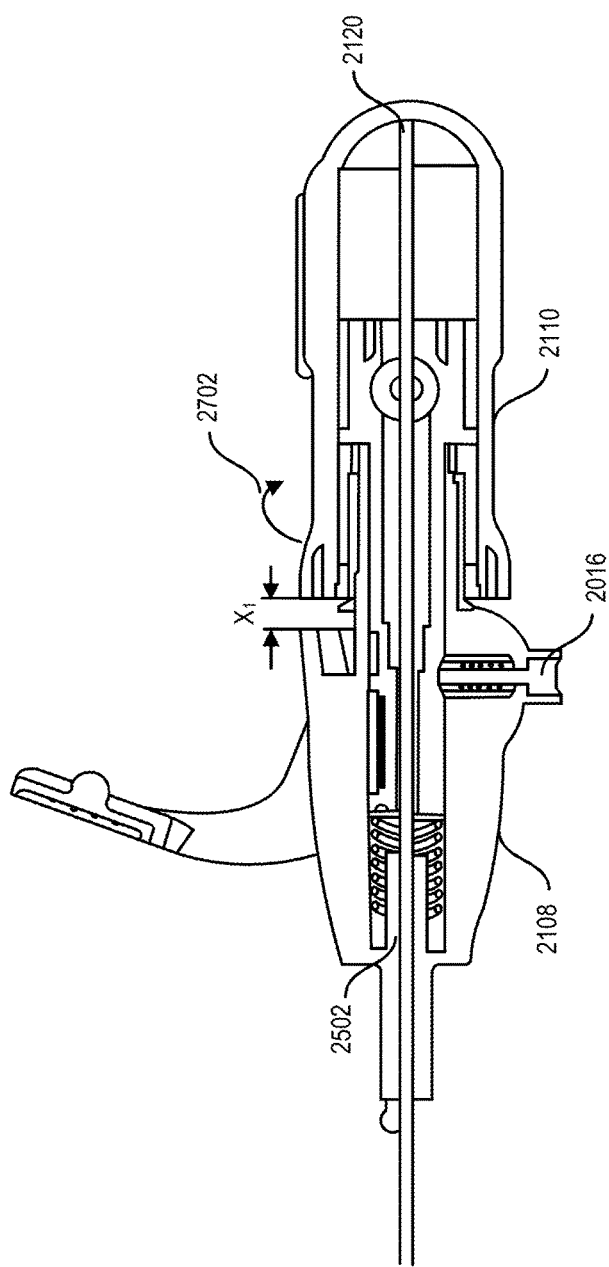
FIG. 30 is a side cross-sectional view of the handle assembly of FIG. 26 during deployment of a first set of wings of the implant.

In accordance with an exemplary method of operating the actuator 2100 to deploy a first set of wings of the implant 2104 (e.g., distal wings 2624b shown in FIG. 27), the body rear 2110 is rotated via a first rotation stroke in a first direction (e.g., clockwise) indicated by an arrow 2702 in FIG. 30 about the longitudinal axis A of the handle assembly 2102. The body rear 2110 is rotated clockwise so that the body rear tab 2402 slides along the outer flange 2128d of the ring connector 2128. As a result of the rotation and movement of the body rear tab 2402 with respect to the ring connector 2128, the distal wings 2624b of the implant 2104 expand outwardly.

The outer flange 2128d of the ring connector is configured such that the body rear tab 2402 can slide along the outer flange 2128d through the first rotation stroke until, at the end of the first rotation stroke, the body rear tab 2402 aligns with an opening 2028 in the ring connector 2128, as shown in FIG. 31A. Force F1 applied by a biasing mechanism, such as the compression spring 2142, moves the body rear tab 2402 through the opening 2028. When body rear tab 2402 is aligned with the opening 2028 in the ring connector 2128 at the end of the first rotation stroke, the body rear 2110 moves axially away from the body front 2108 by a distance X1, as shown in FIG. 30.

Simultaneously with the body rear tab 2402 sliding along the outer flange 2128d of the ring connector 2128, the guide pin 2016 is positioned relative to the actuator base 2126 so that it abuts the corner protrusion 2026 formed on the proximal end of the mid-portion 2126m of the actuator base 2126, as shown in FIGS. 31B and 31C. When the guide pin 2016 is positioned against the corner protrusion 2026 (FIG. 31C), at the end of the rotation stroke, the body rear 2110 is prevented from being moved further axially and it is also prevented from further rotation in the first direction.

As the body rear 2110 moves through the first rotation stroke, the guide wire 2120 attached thereto also moves in the same manner. In this way, as the body rear 2110 is rotated in the first direction and is moved axially away from the body front 2108, the guide wire 2120 follows these movements and, as a result, causes the distal wings 2624b to move to their final configuration as shown in FIG. 27.

After the first set of wings of the implant 2104, such as the distal wings 2624b, are deployed, the handle assembly 2102 can be further operated to cause the second set of wings of the implant 2104, such as the proximal wings 2624a, to deploy. In some embodiments, to deploy the proximal wings 2624a, the body rear 2110 is rotated about the longitudinal axis A of the handle assembly 2102 via a second rotation stroke in a second direction (e.g., counterclockwise) indicated by an arrow 2902 in FIG. 32. Deployment of the proximal wings 2624a can require more than one full rotation of the body rear 2110 with respect to the body front 2108. The rotation of the body rear 2110 in the second direction causes the proximal wings 2624a to expand outward.

Figure 32:
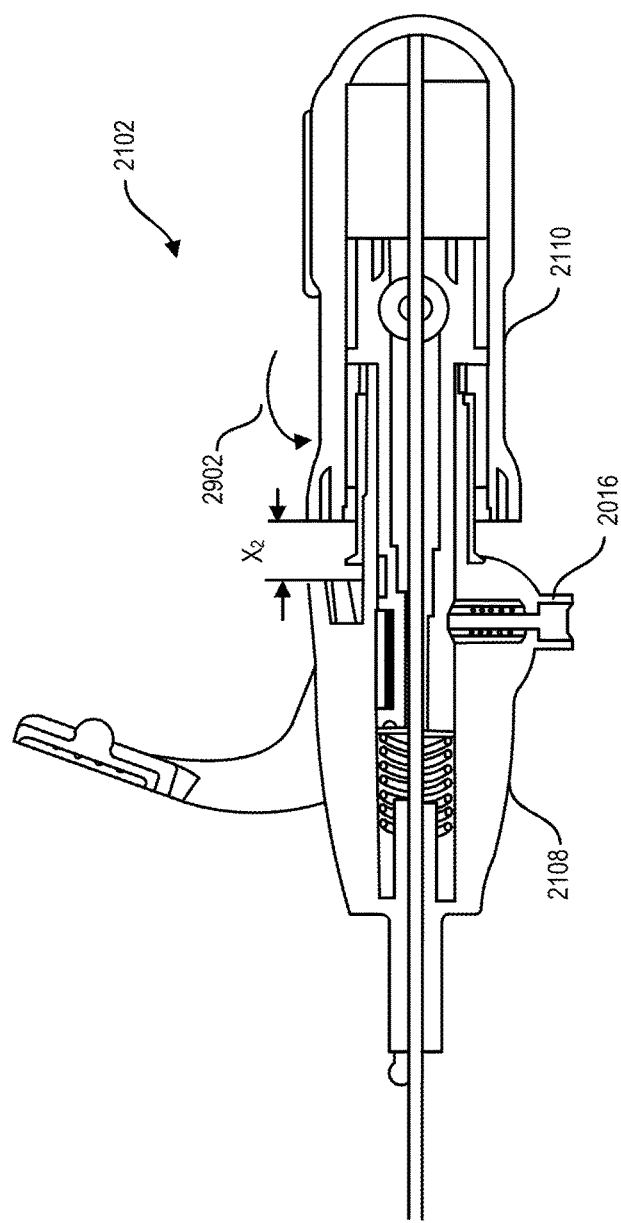
FIG. 32 is side cross-sectional view of the handle assembly of FIG. 30 during deployment of a second set of wings of the implant.
Figure 33A:
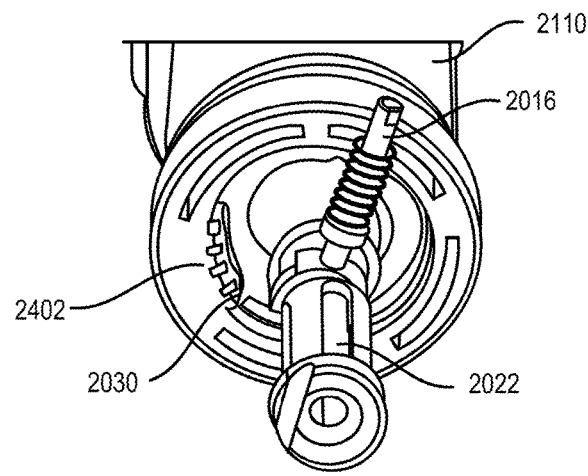
FIG. 33A is a perspective view of a body rear of a housing of the handle assembly of FIG. 32 during deployment of the second set of wings of the implant.
Figure 33B:
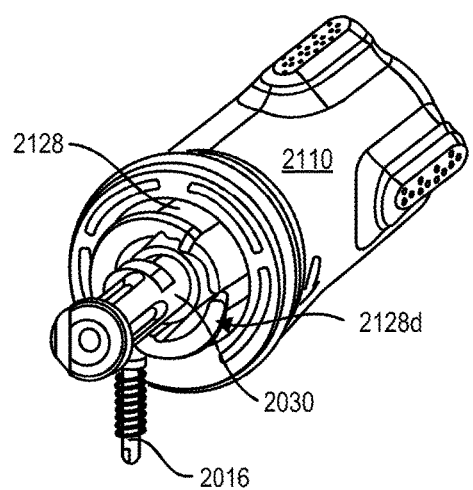
FIG. 33B is another perspective view of a body rear of a housing of the handle assembly of FIG. 32 following deployment of the second set of wings of the implant.
Figure 33C:
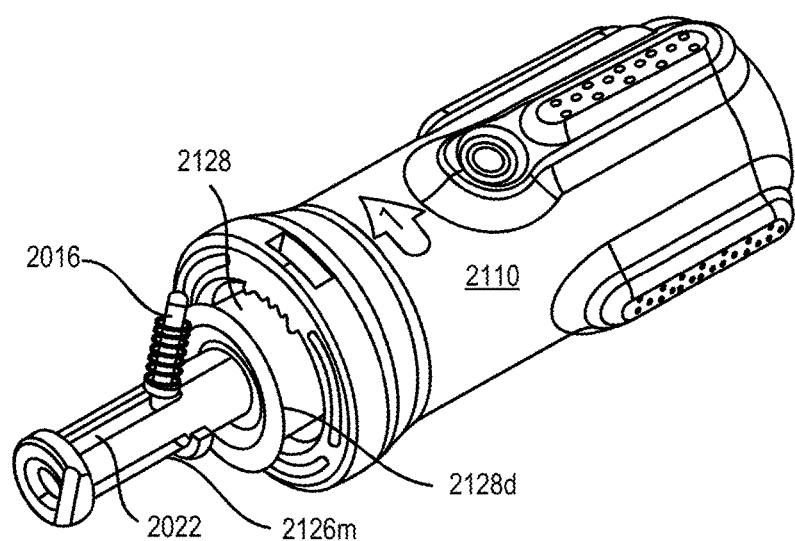
FIG. 33C is another perspective view of a body rear of a housing of the handle assembly of FIG. 32 following deployment of the second set of wings of the implant.

As the body rear 2110 is rotated, a ramp 2030, circumferentially formed around the mid-portion 2126m of the actuator base 2126m and having a gradually increasing height (e.g., in the second, counterclockwise direction), allows the guide pin 2016 to advance over the corner protrusion 2026 during each full rotation of the body rear 2110, as shown in FIG. 33A. The force applied by the compression spring 2142 to the body rear 2110 causes the body rear 2110 to further slide axially away from the body front 2108 during one or more rotations of the second rotation stroke, as shown in FIG. 33B. In this way, the body rear 2110 can be axially spaced away from the body front 2108 by a distance X2 as shown in FIG. 32. This axial movement of the body rear 2110 away from the body front 2108 also causes the guide wire 2120 to move proximally by the same distance, which, in turn, causes the proximal wings 2624a to move into their final configuration shown in FIG. 27.

Once the proximal wings 2624a are fully formed and when the guide pin 2016 is advanced over the corner protrusion 2026, the guide pin spring 2018 pushes the guide pin 2016 into one of the longitudinal tracks 2022 in the actuator base 2126, as shown in FIG. 32C. In this way, the body rear 2110 is prevented from being rotated in both the first and second directions.

Figure 34:
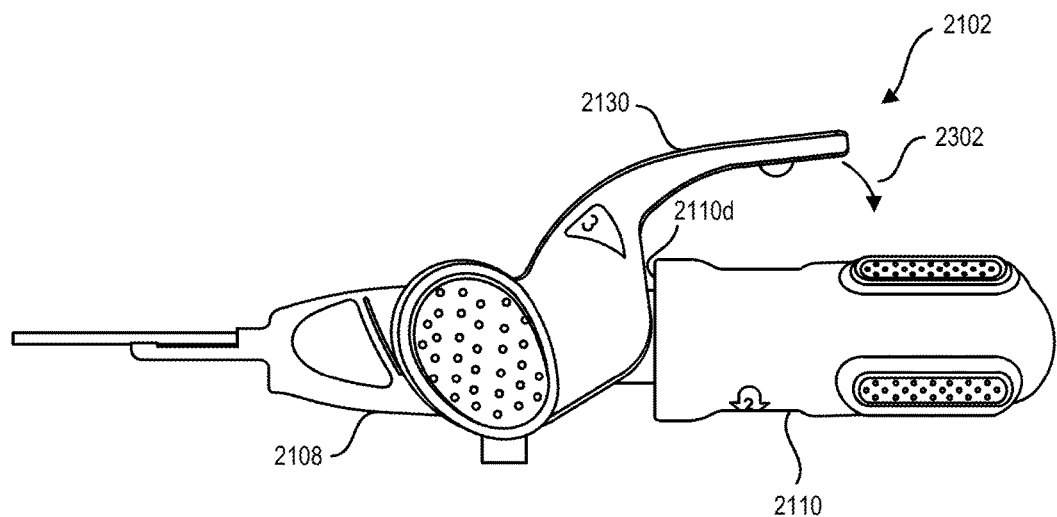
FIG. 34 is a side view of the handle assembly of FIG. 21 during ejection of the implant from the actuator.

After the proximal and distal wings 2624a, 2624b of the implant 2104 are deployed, the implant 2104 is ejected from the actuator 2100 such that the implant 2104 can remain at the surgical site to seal the tissue puncture. In some embodiments, to eject the implant 2104 from the actuator 2100, the lever 2130 coupled to the housing 2101 can be moved proximally in a direction shown by a directional arrow 2302 in FIG. 34. The lever 2130 applies a compressive load to the distal end 2110d of the body rear 2110 so that the rotation of the lever 2130 causes the body rear 2110 to further slide axially away from the body front 108. As a result, the body rear 2110 is further spaced axially apart from the body front 2108 by a distance that is greater than the distance X2 shown in FIG. 32. Although not shown, in one embodiment, as the lever 2130 is being activated, the body rear tab 2402 positioned in a slot (not shown) of the ring connector 2128 can proximally slide within that slot.

As the body rear 2110 slides axially away from the body front 2108, the guide wire 2120 attached to the body rear 110 also moves proximally. In one exemplary embodiment, as discussed above, the guide wire 2120 is coupled at the distal end thereof to the ejection tube 2650 of the implant 2104 which, in turn, is coupled to the core pin 2630. Thus, the tension applied to the guide wire 2120 as a result of the force applied by the lever 2130 to the body rear 2110 causes the core pin 2630 to move proximally against the distal end 2106d of the guide tube 2106. As the lever 2130 is rotated further towards the completion of its rotation, the increased tension on the guide wire 2120 leads to the increased compression force between the core pin 630 and the guide tube 2106 at a location indicated by a numerical reference 2680 in FIG. 27. When the force applied to guide wire 2120 exceeds a certain threshold force, the ejection tube 2650 attached at a proximal end thereof to the guide wire 2120 breaks into two portions at a frangible location. For example, in one embodiment, the ejection tube 2650 is separated at the frangible location 2654 (FIG. 27) into an implant portion 2650i that remains with the deployed implant, and a removable portion 2650r.

Figure 35:
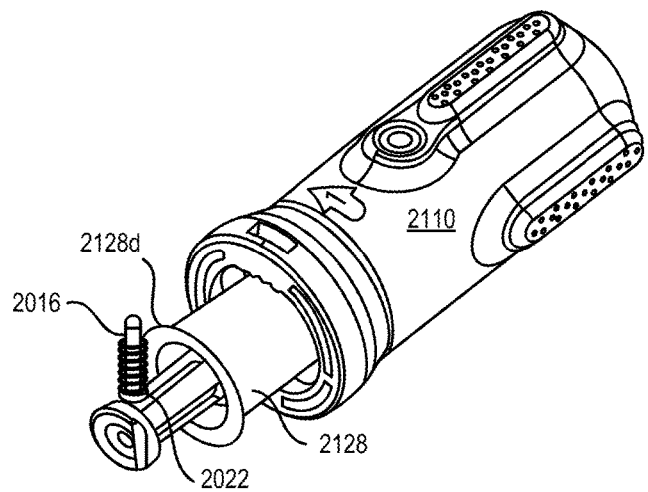
FIG. 35 is a perspective view of a body rear of a housing of the handle assembly of FIG. 34.

In one illustrated embodiment, when the lever 2130 is operated, the guide pin 2016 slides within the guide track 2022 in the actuator base 2126 until it reaches a distal end of the guide track 2022, as shown in FIG. 35. Once the guide pin 2016 is seated within the guide track 2022 in this manner, further movement of the body rear 2110 axially away from the body front 2108 is prevented. After the implant 2104 is ejected, the actuator 2100 can be removed from the surgical site.

It should be appreciated that illustrated methods and devices can be used to deploy implants in any surgical context. One or more components of implant 104 or 2104 can occlude natural or surgically created openings or tissue punctures. Thus, the methods and devices can be used to seal tissue punctures created during catheterization and interventional procedures, such as angioplasty or stenting. The described methods and devices can also be used to seal a fallopian tube to provide a form of birth control or disease prevention, to repair a defect in a heart valve (e.g., a mitral valve), to percutaneously seal a vascular puncture, or seal any opening in a body related to any defect or disease.

Furthermore, although an implant can be deployed using the described methods and devices to occlude an opening in a subject's body, alternatively, in some embodiments, it can be used to promote a flow of fluid through an opening or conduit.

The devices described herein can be designed to be disposed of after a single use, or they can be designed to be used multiple times. In either case, however, a device, such as an actuator, can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

In some embodiments, the systems and devices described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that any system(s) or device(s) in accordance with the described embodiments are sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An actuator for deploying an implant, comprising:
a housing having proximal and distal portions, the proximal portion being rotatable relative to the distal portion about a longitudinal axis of the housing extending through the proximal and distal portions;
a guide tube coupled to the distal portion and having a distal end configured to engage an implant; and
a guide wire extending through the guide tube, the distal portion, and the proximal portion, the guide wire being fixedly coupled to the proximal portion such that rotation of the proximal portion causes the guide wire to rotate;
wherein the proximal portion of the housing is configured to slide axially away from the distal portion after the proximal portion is rotated through a rotation stroke.

2. The actuator of claim 1, further comprising a biasing mechanism configured to cause the proximal portion to slide axially away from the distal portion at the end of the rotation stroke.

3. The actuator of claim 1, wherein the rotation stroke comprises a first rotation stroke in which the proximal portion is rotated in a first direction about the longitudinal axis, and a second rotation stroke in which the proximal portion is rotated in a second opposite direction about the longitudinal axis.

4. The actuator of claim 3, wherein the proximal portion is configured to slide axially away from the distal portion at the end of each of the first rotation stroke and the second rotation stroke.

5. The actuator of claim 1, further comprising a locking mechanism configured to prevent rotation of the proximal portion after an implant coupled to the guide tube is deployed.

6. The actuator of claim 5, wherein the locking mechanism comprises a tab that blocks movement of a guide pin formed on the distal portion.

7. The actuator of claim 1, wherein the proximal portion includes a guide pin that extends into a track for guiding rotational movement of the proximal portion.

8. The actuator of claim 7, wherein the track includes a first portion extending radially about the longitudinal axis, a second portion extending radially about the longitudinal axis, and a third portion extending longitudinally relative to the longitudinal axis and extending between the first and second portions.

9. The actuator of claim 1, further comprising a lever coupled to the housing and operable to move the proximal portion of the housing axially away from the distal portion of the housing and to detach at least a portion of an implant from the guide tube.

10. The actuator of claim 1, wherein the proximal portion is configured to rotate in a first direction to deploy a first portion of the implant, and in a second opposite direction to deploy a second portion of the implant.

11. The actuator of claim 1, wherein the proximal portion is configured to be prevented from rotating in the first direction after the first portion of the implant is deployed, and the proximal portion is configured to be prevented from rotating in the second direction after the second portion of the implant is deployed.

12. The actuator of claim 11, wherein the proximal portion is configured to be prevented from rotating in the first and second directions after the first and second portions of the implant are deployed.

13. An actuator assembly for deploying an implant, comprising:
a handle assembly having a guide tube extending distally therefrom, the guide tube having a distal end configured to engage an implant;
a guide wire extending through the guide tube and at least a portion of the handle assembly;
a rotatable actuator coupled to the handle assembly and configured to rotate the guide wire; and
a locking mechanism configured to prevent rotation of the rotatable actuator after an implant coupled to the guide tube is deployed.

14. The actuator assembly of claim 13, further comprising a lever coupled to the handle assembly and operable to detach at least a portion of an implant from the guide tube.

15. The actuator assembly of claim 13, wherein the rotatable actuator is configured to rotate in a first direction to deploy a first portion of an implant, and in a second, opposite direction to deploy a second portion of an implant.

16. The actuator assembly of claim 15, wherein the rotatable actuator is prevented from rotating in the first direction after the first portion of the implant is deployed, and the rotatable actuator is prevented from rotating in the second direction after the second portion of the implant is deployed.

17. The actuator assembly of claim 16, wherein the rotatable actuator is configured to rotate in both a clockwise direction and a counterclockwise direction to deploy an implant.

18. The actuator assembly of claim 13, wherein the rotatable actuator is configured to slide axially away from a distal portion of the handle assembly.

19. The actuator assembly of claim 18, further comprising a biasing mechanism configured to bias the rotatable actuator in a proximal direction relative to the housing.

20. The actuator assembly of claim 13, wherein the rotatable actuator is configured to slide axially relative to the handle at the end of a rotation stroke.

21. A method for deploying an implant, comprising:
manipulating a delivery device to position an implant at a surgical site;
rotating an actuator of a handle assembly of the delivery device through a first rotation stroke to deploy a first portion of the implant; and
rotating the actuator of the handle assembly through a second rotation stroke to deploy a second portion of the implant, the actuator being prevented from rotating upon completion of the second rotation stroke wherein the actuator is rotated in a first direction for the first rotation stroke, and the actuator is rotated in a second opposite direction for the second rotation stroke.

22. The method of claim 21, wherein the actuator slides longitudinally upon completion of the first rotation stroke.

23. The method of claim 21, wherein the actuator slides longitudinally upon completion of each of the first rotation stroke and the second rotation stroke.

24. The method of claim 21, further comprising rotating a lever on the handle assembly to detach at least a portion of the implant from the delivery device.

* * * * *